(12) United States Patent
Pfeil et al.

(10) Patent No.: US 8,663,942 B2
(45) Date of Patent: *Mar. 4, 2014

(54) MEANS AND METHODS FOR THE DETERMINATION OF THE AMOUNT OF NEUROTOXIN POLYPEPTIDE AND OF ITS CATALYTIC AND PROTEOLYTIC ACTIVITIES

(75) Inventors: Michael Pfeil, Konigstein (DE); Josef Friedrich, Rauenberg (DE)

(73) Assignee: Merz Pharma GmbH & Co. KGaA, Frankfurt am Main (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/138,948

(22) PCT Filed: Apr. 23, 2010

(86) PCT No.: PCT/EP2010/055432
§ 371 (c)(1),
(2), (4) Date: Jan. 26, 2012

(87) PCT Pub. No.: WO2010/124998
PCT Pub. Date: Nov. 4, 2010

(65) Prior Publication Data
US 2012/0142024 A1    Jun. 7, 2012

Related U.S. Application Data

(60) Provisional application No. 61/214,650, filed on Apr. 27, 2009.

(30) Foreign Application Priority Data

Apr. 27, 2009 (EP) .................................... 09158788

(51) Int. Cl.
*G01N 33/53* (2006.01)
*G01N 33/536* (2006.01)
*G01N 33/566* (2006.01)
*C07K 16/00* (2006.01)

(52) U.S. Cl.
USPC ....... 435/7.9; 436/501; 435/278.2; 530/388.2

(58) Field of Classification Search
None
See application file for complete search history.

(56) References Cited

U.S. PATENT DOCUMENTS 5,677,182 A * 10/1997 Kriegler et al. ............... 435/335
2012/0004179 A1 * 1/2012 Pfeil et al. .................... 514/18.1

FOREIGN PATENT DOCUMENTS

| WO | WO 02/23195 | | 3/2002 | |
| WO | WO2008/157374 | * | 12/2008 | ............. G01N 33/55 |
| WO | WO2009/014854 | * | 1/2009 | ............. C07K 14/33 |

OTHER PUBLICATIONS

Stanker et al., (J. Immunological Methods; 2008 vol. 336, pp. 1-8).*
Antharavally, 1997, Journal Protein Chem, vol. 16, p. 787-799.
Antharavally, 1998, Journal Protein Chem, vol. 17, p. 417-428.
Beecher, 1997, Journal Proteine Chem, vol. 16, p. 701-712.
Campbell, 1993, Biochim Siophys Acta, vol. 1216, No, 3, p. 487-491.
Couesnon, 2006, Microbilolgy, vol. 152, p. 759-770.
Dressier, 2005, Mov Disorder, vol. 20, p. 1617-1619.
Fischer, 2007, PNAS vol. 104, p. 10447-10452.
Jost, 2007, Drugs, vol. 67, p. 669-683.
Krieglstein 1991, Eur Journal Biochem, vol. 202, p. 41-51.
Krieglstein, 1994, Journal Protein Chem, vol. 12, p. 49-57.
Krieglstein, et al., 1990, Eur Journal Biochem, vol. 199, p. 39-45.
Pearce, 1994, Toxicol Appl Pharmacol, vol. 128, p. 69-77.
Sagane, 1999 Journal Protein Chem, vol. 18, p. 885-892.
Silberstein, Pain Practice 4, S19-S26, 2004.
Written Opinion for PCT/EP2010/055432.
Ferreira J L, et al., Journal of Food Protection, vol. 67, No. 1, p. 230-206 Abstract, Jan. 1, 2004.
International Search Report for PCT/EP2010/055432 of May 28, 2010.
Rasooly Reuven, et al., Applied and Environmnetal Microbiology, vol. 74, No. 14, p. 4309-4313 Abstract, Jul. 1, 2008.

* cited by examiner

*Primary Examiner* — Jacob Cheu
*Assistant Examiner* — Carmencita M Belei
(74) *Attorney, Agent, or Firm* — Hueschen and Sage

(57) ABSTRACT

The present invention pertains to the field of tools for ensuring manufacture of polypeptides and quality control. Specifically, it relates to a method for determining the amount of processed (active) neurotoxin polypeptides in a solution comprising processed neurotoxin polypeptides and partially processed or unprocessed neurotoxin polypeptides. The present invention further relates to a device for determining the amount of neurotoxin polypeptides and a kit adapted to carry out the method of the present invention.

18 Claims, 4 Drawing Sheets

Figure 3:
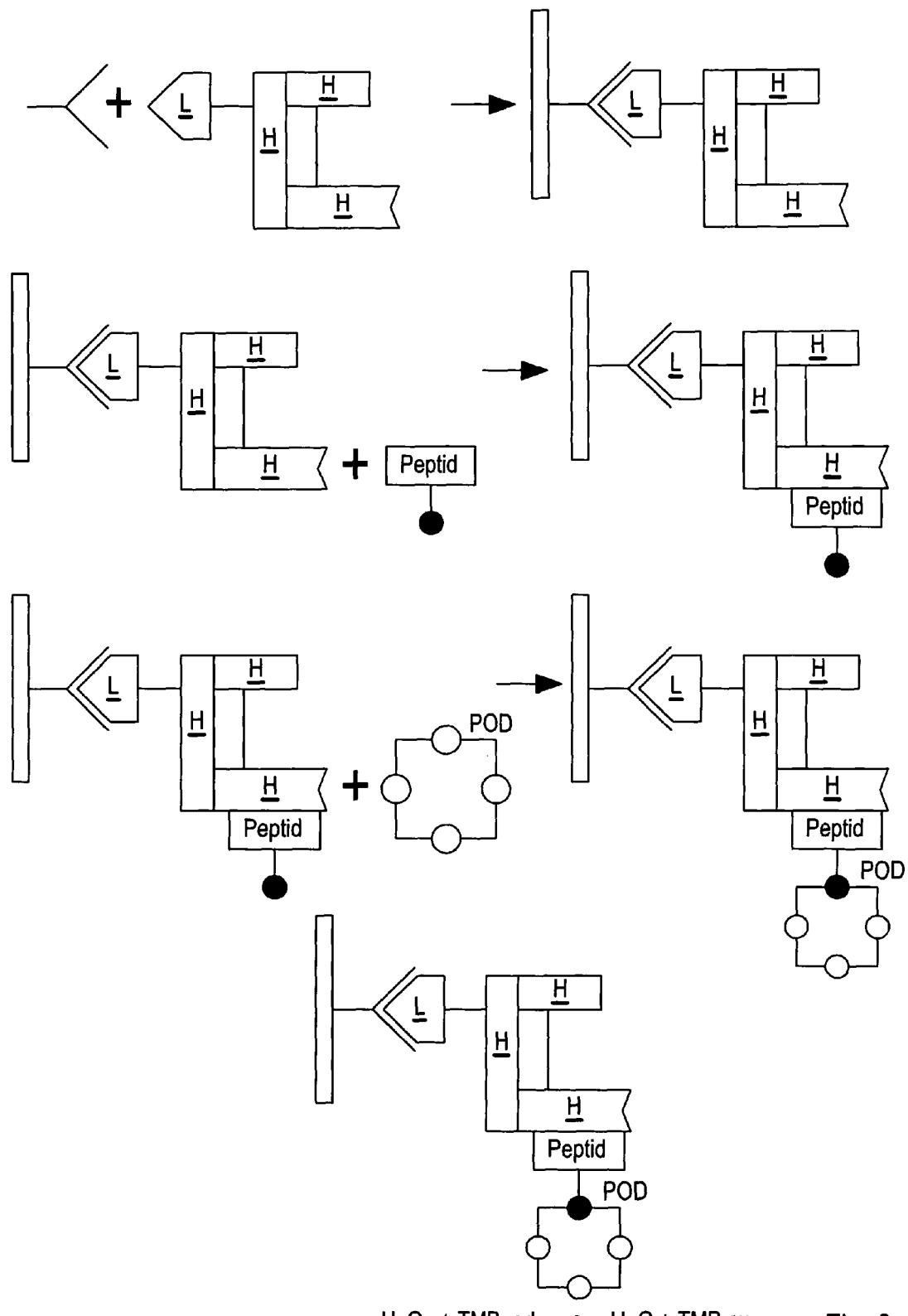

H₂O₂ + TMB red → H₂O + TMB ox    Fig. 3

Peptid-Arg-
p-Nitrophenylanilid  →  Peptid-Arg +
p-Nitrophenylanilin (gelb)

SEQUENCE LISTING

<160> NUMBER OF SEQ ID NOS: 26

<210> SEQ ID NO 1
<211> LENGTH: 31
<212> TYPE: PRT
<213> ORGANISM: Clostridium botulinum

<400> SEQUENCE: 1

Lys Leu Leu Cys Val Arg Gly Ile Ile Thr Ser Lys Thr Lys Ser Leu
1               5                   10                  15

Asp Lys Gly Tyr Asn Lys Ala Leu Asn Asp Leu Cys Ile Lys Val
            20                  25                  30

<210> SEQ ID NO 2
<211> LENGTH: 16
<212> TYPE: PRT
<213> ORGANISM: Clostridium botulinum

<400> SEQUENCE: 2

Ile Gln Met Cys Lys Ser Val Lys Ala Pro Gly Ile Cys Ile Asp Val
1               5                   10                  15

<210> SEQ ID NO 3
<211> LENGTH: 25
<212> TYPE: PRT
<213> ORGANISM: Clostridium botulinum

<400> SEQUENCE: 3

Thr Lys Phe Cys His Lys Ala Ile Asp Gly Arg Ser Leu Tyr Asn Lys
1               5                   10                  15

Thr Leu Asp Cys Arg Glu Leu Leu Val
            20                  25

```
<210> SEQ ID NO 4
<211> LENGTH: 20
<212> TYPE: PRT
<213> ORGANISM: Clostridium botulinum

<400> SEQUENCE: 4

Thr Lys Val Cys Leu Arg Leu Thr Lys Asn Ser Arg Asp Asp Ser Thr
1               5                   10                  15

Cys Ile Lys Val
            20

<210> SEQ ID NO 5
<211> LENGTH: 21
<212> TYPE: PRT
<213> ORGANISM: Clostridium botulinum

<400> SEQUENCE: 5

Ile Arg Phe Cys Lys Asn Ile Val Ser Val Lys Gly Ile Arg Lys Ser
1               5                   10                  15

Ile Cys Ile Glu Ile
            20

<210> SEQ ID NO 6
<211> LENGTH: 23
<212> TYPE: PRT
<213> ORGANISM: Clostridium botulinum

<400> SEQUENCE: 6

Val Lys Phe Cys Lys Ser Val Ile Pro Arg Lys Gly Thr Lys Ala Pro
1               5                   10                  15

Pro Arg Leu Cys Ile Arg Val
            20

<210> SEQ ID NO 7
<211> LENGTH: 21
<212> TYPE: PRT
<213> ORGANISM: Clostridium botulinum

<400> SEQUENCE: 7

Ile Ala Met Cys Lys Pro Val Met Tyr Lys Asn Thr Gly Lys Ser Glu
1               5                   10                  15

Gln Cys Ile Ile Val
            20

<210> SEQ ID NO 8
<211> LENGTH: 35
<212> TYPE: PRT
<213> ORGANISM: Clostridium tetani

<400> SEQUENCE: 8

Ile Gly Leu Cys Lys Lys Ile Ile Pro Pro Thr Asn Ile Arg Glu Asn
1               5                   10                  15

Leu Tyr Asn Arg Thr Ala Ser Leu Thr Asp Leu Gly Gly Glu Leu Cys
            20                  25                  30

Ile Lys Ile
        35

<210> SEQ ID NO 9
<211> LENGTH: 10
<212> TYPE: PRT
<213> ORGANISM: Clostridium botulinum

<400> SEQUENCE: 9
```

```
Thr Lys Ser Leu Asp Lys Gly Tyr Asn Lys
1               5                   10

<210> SEQ ID NO 10
<211> LENGTH: 10
<212> TYPE: PRT
<213> ORGANISM: Clostridium botulinum

<400> SEQUENCE: 10

Cys Lys Ser Val Lys Ala Pro Gly Ile Cys
1               5                   10

<210> SEQ ID NO 11
<211> LENGTH: 5
<212> TYPE: PRT
<213> ORGANISM: Clostridium botulinum

<400> SEQUENCE: 11

Ser Leu Tyr Asn Lys
1               5

<210> SEQ ID NO 12
<211> LENGTH: 3
<212> TYPE: PRT
<213> ORGANISM: Clostridium botulinum

<400> SEQUENCE: 12

Asn Ser Arg
1

<210> SEQ ID NO 13
<211> LENGTH: 3
<212> TYPE: PRT
<213> ORGANISM: Clostridium botulinum

<400> SEQUENCE: 13

Gly Ile Arg
1

<210> SEQ ID NO 14
<211> LENGTH: 4
<212> TYPE: PRT
<213> ORGANISM: Clostridium botulinum

<400> SEQUENCE: 14

Lys Gly Thr Lys
1

<210> SEQ ID NO 15
<211> LENGTH: 4
<212> TYPE: PRT
<213> ORGANISM: Clostridium botulinum

<400> SEQUENCE: 15

Asn Gly Thr Lys
1

<210> SEQ ID NO 16
<211> LENGTH: 6
<212> TYPE: PRT
<213> ORGANISM: Clostridium tetani

<400> SEQUENCE: 16

Glu Asn Leu Tyr Asn Arg
1               5
```

<210> SEQ ID NO 17
<211> LENGTH: 1296
<212> TYPE: PRT
<213> ORGANISM: Clostridium botulinum

<400> SEQUENCE: 17

Met Pro Phe Val Asn Lys Gln Phe Asn Tyr Lys Asp Pro Val Asn Gly
1               5                   10                  15

Val Asp Ile Ala Tyr Ile Lys Ile Pro Asn Ala Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Glu Glu Gly Asp Leu Asn Pro Pro Pro Glu
    50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
    130                 135                 140

Arg Ser Glu Glu Leu Asn Leu Val Ile Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Glu
    210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
            260                 265                 270

Phe Ile Asp Ser Leu Gln Glu Asn Glu Phe Arg Leu Tyr Tyr Tyr Asn
        275                 280                 285

Lys Phe Lys Asp Ile Ala Ser Thr Leu Asn Lys Ala Lys Ser Ile Val
    290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
                325                 330                 335

Lys Phe Asp Lys Leu Tyr Lys Met Leu Thr Glu Ile Tyr Thr Glu Asp
            340                 345                 350

Asn Phe Val Lys Phe Phe Lys Val Leu Asn Arg Lys Thr Tyr Leu Asn
        355                 360                 365

Phe Asp Lys Ala Val Phe Lys Ile Asn Ile Val Pro Lys Val Asn Tyr
    370                 375                 380

```
Thr Ile Tyr Asp Gly Phe Asn Leu Arg Asn Thr Asn Leu Ala Ala Asn
385                 390                 395                 400

Phe Asn Gly Gln Asn Thr Glu Ile Asn Asn Met Asn Phe Thr Lys Leu
            405                 410                 415

Lys Asn Phe Thr Gly Leu Phe Glu Phe Tyr Lys Leu Leu Cys Val Arg
            420                 425                 430

Gly Ile Ile Thr Ser Lys Thr Lys Ser Leu Asp Lys Gly Tyr Asn Lys
            435                 440                 445

Ala Leu Asn Asp Leu Cys Ile Lys Val Asn Asn Trp Asp Leu Phe Phe
450                 455                 460

Ser Pro Ser Glu Asp Asn Phe Thr Asn Asp Leu Asn Lys Gly Glu Glu
465                 470                 475                 480

Ile Thr Ser Asp Thr Asn Ile Glu Ala Ala Glu Glu Asn Ile Ser Leu
            485                 490                 495

Asp Leu Ile Gln Gln Tyr Tyr Leu Thr Phe Asn Phe Asp Asn Glu Pro
            500                 505                 510

Glu Asn Ile Ser Ile Glu Asn Leu Ser Ser Asp Ile Gly Gln Leu
            515                 520                 525

Glu Leu Met Pro Asn Ile Glu Arg Phe Pro Asn Gly Lys Lys Tyr Glu
530                 535                 540

Leu Asp Lys Tyr Thr Met Phe His Tyr Leu Arg Ala Gln Glu Phe Glu
545                 550                 555                 560

His Gly Lys Ser Arg Ile Ala Leu Thr Asn Ser Val Asn Glu Ala Leu
            565                 570                 575

Leu Asn Pro Ser Arg Val Tyr Thr Phe Phe Ser Ser Tyr Val Lys
            580                 585                 590

Lys Val Asn Lys Ala Thr Glu Ala Ala Met Phe Leu Gly Trp Val Glu
            595                 600                 605

Gln Leu Val Tyr Asp Phe Thr Asp Glu Thr Ser Glu Val Ser Thr Thr
            610                 615                 620

Asp Lys Ile Ala Asp Ile Thr Ile Ile Pro Tyr Ile Gly Pro Ala
625                 630                 635                 640

Leu Asn Ile Gly Asn Met Leu Tyr Lys Asp Asp Phe Val Gly Ala Leu
            645                 650                 655

Ile Phe Ser Gly Ala Val Ile Leu Leu Glu Phe Ile Pro Glu Ile Ala
            660                 665                 670

Ile Pro Val Leu Gly Thr Phe Ala Leu Val Ser Tyr Ile Ala Asn Lys
            675                 680                 685

Val Leu Thr Val Gln Thr Ile Asp Asn Ala Leu Ser Lys Arg Asn Glu
            690                 695                 700

Lys Trp Asp Glu Val Tyr Lys Tyr Ile Val Thr Asn Trp Leu Ala Lys
705                 710                 715                 720

Val Asn Thr Gln Ile Asp Leu Ile Arg Lys Lys Met Lys Glu Ala Leu
            725                 730                 735

Glu Asn Gln Ala Glu Ala Thr Lys Ala Ile Ile Asn Tyr Gln Tyr Asn
            740                 745                 750

Gln Tyr Thr Glu Glu Lys Asn Asn Ile Asn Phe Asn Ile Asp Asp
            755                 760                 765

Leu Ser Ser Lys Leu Asn Glu Ser Ile Asn Lys Ala Met Ile Asn Ile
770                 775                 780

Asn Lys Phe Leu Asn Gln Cys Ser Val Ser Tyr Leu Met Asn Ser Met
785                 790                 795                 800

Ile Pro Tyr Gly Val Lys Arg Leu Glu Asp Phe Asp Ala Ser Leu Lys
            805                 810                 815
```

```
Asp Ala Leu Leu Lys Tyr Ile Tyr Asp Asn Arg Gly Thr Leu Ile Gly
            820                 825                 830

Gln Val Asp Arg Leu Lys Asp Lys Val Asn Asn Thr Leu Ser Thr Asp
        835                 840                 845

Ile Pro Phe Gln Leu Ser Lys Tyr Val Asp Asn Gln Arg Leu Leu Ser
    850                 855                 860

Thr Phe Thr Glu Tyr Ile Lys Asn Ile Ile Asn Thr Ser Ile Leu Asn
865                 870                 875                 880

Leu Arg Tyr Glu Ser Asn His Leu Ile Asp Leu Ser Arg Tyr Ala Ser
                885                 890                 895

Lys Ile Asn Ile Gly Ser Lys Val Asn Phe Asp Pro Ile Asp Lys Asn
                900                 905                 910

Gln Ile Gln Leu Phe Asn Leu Glu Ser Ser Lys Ile Glu Val Ile Leu
            915                 920                 925

Lys Asn Ala Ile Val Tyr Asn Ser Met Tyr Glu Asn Phe Ser Thr Ser
        930                 935                 940

Phe Trp Ile Arg Ile Pro Lys Tyr Phe Asn Ser Ile Ser Leu Asn Asn
945                 950                 955                 960

Glu Tyr Thr Ile Ile Asn Cys Met Glu Asn Asn Ser Gly Trp Lys Val
                965                 970                 975

Ser Leu Asn Tyr Gly Glu Ile Ile Trp Thr Leu Gln Asp Thr Gln Glu
                980                 985                 990

Ile Lys Gln Arg Val Val Phe Lys Tyr Ser Gln Met Ile Asn Ile Ser
            995                1000                1005

Asp Tyr Ile Asn Arg Trp Ile Phe Val Thr Ile Thr Asn Asn Arg
            1010                1015                1020

Leu Asn Asn Ser Lys Ile Tyr Ile Asn Gly Arg Leu Ile Asp Gln
            1025                1030                1035

Lys Pro Ile Ser Asn Leu Gly Asn Ile His Ala Ser Asn Asn Ile
            1040                1045                1050

Met Phe Lys Leu Asp Gly Cys Arg Asp Thr His Arg Tyr Ile Trp
            1055                1060                1065

Ile Lys Tyr Phe Asn Leu Phe Asp Lys Glu Leu Asn Glu Lys Glu
            1070                1075                1080

Ile Lys Asp Leu Tyr Asp Asn Gln Ser Asn Ser Gly Ile Leu Lys
            1085                1090                1095

Asp Phe Trp Gly Asp Tyr Leu Gln Tyr Asp Lys Pro Tyr Tyr Met
            1100                1105                1110

Leu Asn Leu Tyr Asp Pro Asn Lys Tyr Val Asp Val Asn Asn Val
            1115                1120                1125

Gly Ile Arg Gly Tyr Met Tyr Leu Lys Gly Pro Arg Gly Ser Val
            1130                1135                1140

Met Thr Thr Asn Ile Tyr Leu Asn Ser Ser Leu Tyr Arg Gly Thr
            1145                1150                1155

Lys Phe Ile Ile Lys Lys Tyr Ala Ser Gly Asn Lys Asp Asn Ile
            1160                1165                1170

Val Arg Asn Asn Asp Arg Val Tyr Ile Asn Val Val Val Lys Asn
            1175                1180                1185

Lys Glu Tyr Arg Leu Ala Thr Asn Ala Ser Gln Ala Gly Val Glu
            1190                1195                1200

Lys Ile Leu Ser Ala Leu Glu Ile Pro Asp Val Gly Asn Leu Ser
            1205                1210                1215

Gln Val Val Val Met Lys Ser Lys Asn Asp Gln Gly Ile Thr Asn
```

```
                  1220             1225            1230
  Lys Cys Lys Met Asn Leu Gln  Asp Asn Asn Gly Asn  Asp Ile Gly
          1235            1240                1245

Phe Ile Gly Phe His Gln Phe  Asn Asn Ile Ala Lys  Leu Val Ala
      1250            1255                1260

Ser Asn Trp Tyr Asn Arg Gln  Ile Glu Arg Ser Ser  Arg Thr Leu
          1265            1270                1275

Gly Cys Ser Trp Glu Phe Ile  Pro Val Asp Asp Gly  Trp Gly Glu
          1280            1285                1290

Arg Pro Leu
          1295

<210> SEQ ID NO 18
<211> LENGTH: 1291
<212> TYPE: PRT
<213> ORGANISM: Clostridium botulinum

<400> SEQUENCE: 18

Met Pro Val Thr Ile Asn Asn Phe Asn Tyr Asn Asp Pro Ile Asp Asn
1               5                   10                  15

Asn Asn Ile Ile Met Met Glu Pro Pro Phe Ala Arg Gly Thr Gly Arg
            20                  25                  30

Tyr Tyr Lys Ala Phe Lys Ile Thr Asp Arg Ile Trp Ile Ile Pro Glu
        35                  40                  45

Arg Tyr Thr Phe Gly Tyr Lys Pro Glu Asp Phe Asn Lys Ser Ser Gly
    50                  55                  60

Ile Phe Asn Arg Asp Val Cys Glu Tyr Tyr Asp Pro Asp Tyr Leu Asn
65                  70                  75                  80

Thr Asn Asp Lys Lys Asn Ile Phe Leu Gln Thr Met Ile Lys Leu Phe
                85                  90                  95

Asn Arg Ile Lys Ser Lys Pro Leu Gly Glu Lys Leu Leu Glu Met Ile
            100                 105                 110

Ile Asn Gly Ile Pro Tyr Leu Gly Asp Arg Arg Val Pro Leu Glu Glu
        115                 120                 125

Phe Asn Thr Asn Ile Ala Ser Val Thr Val Asn Lys Leu Ile Ser Asn
    130                 135                 140

Pro Gly Glu Val Glu Arg Lys Lys Gly Ile Phe Ala Asn Leu Ile Ile
145                 150                 155                 160

Phe Gly Pro Gly Pro Val Leu Asn Glu Asn Glu Thr Ile Asp Ile Gly
                165                 170                 175

Ile Gln Asn His Phe Ala Ser Arg Glu Gly Phe Gly Gly Ile Met Gln
            180                 185                 190

Met Lys Phe Cys Pro Glu Tyr Val Ser Val Phe Asn Asn Val Gln Glu
        195                 200                 205

Asn Lys Gly Ala Ser Ile Phe Asn Arg Arg Gly Tyr Phe Ser Asp Pro
    210                 215                 220

Ala Leu Ile Leu Met His Glu Leu Ile His Val Leu His Gly Leu Tyr
225                 230                 235                 240

Gly Ile Lys Val Asp Asp Leu Pro Ile Val Pro Asn Glu Lys Lys Phe
                245                 250                 255

Phe Met Gln Ser Thr Asp Ala Ile Gln Ala Glu Glu Leu Tyr Thr Phe
            260                 265                 270

Gly Gly Gln Asp Pro Ser Ile Ile Thr Pro Ser Thr Asp Lys Ser Ile
        275                 280                 285

Tyr Asp Lys Val Leu Gln Asn Phe Arg Gly Ile Val Asp Arg Leu Asn
```

```
                290                 295                 300
Lys Val Leu Val Cys Ile Ser Asp Pro Asn Ile Asn Ile Asn Ile Tyr
305                 310                 315                 320

Lys Asn Lys Phe Lys Asp Lys Tyr Lys Phe Val Glu Asp Ser Glu Gly
                325                 330                 335

Lys Tyr Ser Ile Asp Val Glu Ser Phe Asp Lys Leu Tyr Lys Ser Leu
                340                 345                 350

Met Phe Gly Phe Thr Glu Thr Asn Ile Ala Glu Asn Tyr Lys Ile Lys
                355                 360                 365

Thr Arg Ala Ser Tyr Phe Ser Asp Ser Leu Pro Pro Val Lys Ile Lys
370                 375                 380

Asn Leu Leu Asp Asn Glu Ile Tyr Thr Ile Glu Gly Phe Asn Ile
385                 390                 395                 400

Ser Asp Lys Asp Met Glu Lys Glu Tyr Arg Gly Gln Asn Lys Ala Ile
                405                 410                 415

Asn Lys Gln Ala Tyr Glu Glu Ile Ser Lys Glu His Leu Ala Val Tyr
                420                 425                 430

Lys Ile Gln Met Cys Lys Ser Val Lys Ala Pro Gly Ile Cys Ile Asp
                435                 440                 445

Val Asp Asn Glu Asp Leu Phe Phe Ile Ala Asp Lys Asn Ser Phe Ser
450                 455                 460

Asp Asp Leu Ser Lys Asn Glu Arg Ile Glu Tyr Asn Thr Gln Ser Asn
465                 470                 475                 480

Tyr Ile Glu Asn Asp Phe Pro Ile Asn Glu Leu Ile Leu Asp Thr Asp
                485                 490                 495

Leu Ile Ser Lys Ile Glu Leu Pro Ser Glu Asn Thr Glu Ser Leu Thr
                500                 505                 510

Asp Phe Asn Val Asp Val Pro Val Tyr Glu Lys Gln Pro Ala Ile Lys
                515                 520                 525

Lys Ile Phe Thr Asp Glu Asn Thr Ile Phe Gln Tyr Leu Tyr Ser Gln
                530                 535                 540

Thr Phe Pro Leu Asp Ile Arg Asp Ile Ser Leu Thr Ser Ser Phe Asp
545                 550                 555                 560

Asp Ala Leu Leu Phe Ser Asn Lys Val Tyr Ser Phe Ser Met Asp
                565                 570                 575

Tyr Ile Lys Thr Ala Asn Lys Val Val Glu Ala Gly Leu Phe Ala Gly
                580                 585                 590

Trp Val Lys Gln Ile Val Asn Asp Phe Val Ile Glu Ala Asn Lys Ser
                595                 600                 605

Asn Thr Met Asp Lys Ile Ala Asp Ile Ser Leu Ile Val Pro Tyr Ile
610                 615                 620

Gly Leu Ala Leu Asn Val Gly Asn Glu Thr Ala Lys Gly Asn Phe Glu
625                 630                 635                 640

Asn Ala Phe Glu Ile Ala Gly Ala Ser Ile Leu Leu Glu Phe Ile Pro
                645                 650                 655

Glu Leu Leu Ile Pro Val Val Gly Ala Phe Leu Leu Glu Ser Tyr Ile
                660                 665                 670

Asp Asn Lys Asn Lys Ile Ile Lys Thr Ile Asp Asn Ala Leu Thr Lys
                675                 680                 685

Arg Asn Glu Lys Trp Ser Asp Met Tyr Gly Leu Ile Val Ala Gln Trp
                690                 695                 700

Leu Ser Thr Val Asn Thr Gln Phe Tyr Thr Ile Lys Glu Gly Met Tyr
705                 710                 715                 720
```

```
Lys Ala Leu Asn Tyr Gln Ala Gln Ala Leu Glu Ile Ile Lys Tyr
                725                 730                 735

Arg Tyr Asn Ile Tyr Ser Glu Lys Glu Lys Ser Asn Ile Asn Ile Asp
                740                 745                 750

Phe Asn Asp Ile Asn Ser Lys Leu Asn Glu Gly Ile Asn Gln Ala Ile
                755                 760                 765

Asp Asn Ile Asn Asn Phe Ile Asn Gly Cys Ser Val Ser Tyr Leu Met
                770                 775                 780

Lys Lys Met Ile Pro Leu Ala Val Glu Lys Leu Leu Asp Phe Asp Asn
785                 790                 795                 800

Thr Leu Lys Lys Asn Leu Leu Asn Tyr Ile Asp Glu Asn Lys Leu Tyr
                805                 810                 815

Leu Ile Gly Ser Ala Glu Tyr Glu Lys Ser Lys Val Asn Lys Tyr Leu
                820                 825                 830

Lys Thr Ile Met Pro Phe Asp Leu Ser Ile Tyr Thr Asn Asp Thr Ile
                835                 840                 845

Leu Ile Glu Met Phe Asn Lys Tyr Asn Ser Glu Ile Leu Asn Asn Ile
                850                 855                 860

Ile Leu Asn Leu Arg Tyr Lys Asp Asn Asn Leu Ile Asp Leu Ser Gly
865                 870                 875                 880

Tyr Gly Ala Lys Val Glu Val Tyr Asp Gly Val Glu Leu Asn Asp Lys
                885                 890                 895

Asn Gln Phe Lys Leu Thr Ser Ser Ala Asn Ser Lys Ile Arg Val Thr
                900                 905                 910

Gln Asn Gln Asn Ile Ile Phe Asn Ser Val Phe Leu Asp Phe Ser Val
                915                 920                 925

Ser Phe Trp Ile Arg Ile Pro Lys Tyr Lys Asn Asp Gly Ile Gln Asn
                930                 935                 940

Tyr Ile His Asn Glu Tyr Thr Ile Ile Asn Cys Met Lys Asn Asn Ser
945                 950                 955                 960

Gly Trp Lys Ile Ser Ile Arg Gly Asn Arg Ile Ile Trp Thr Leu Ile
                965                 970                 975

Asp Ile Asn Gly Lys Thr Lys Ser Val Phe Phe Glu Tyr Asn Ile Arg
                980                 985                 990

Glu Asp Ile Ser Glu Tyr Ile Asn Arg Trp Phe Phe Val Thr Ile Thr
                995                 1000                1005

Asn Asn Leu Asn Asn Ala Lys Ile Tyr Ile Asn Gly Lys Leu Glu
                1010                1015                1020

Ser Asn Thr Asp Ile Lys Asp Ile Arg Glu Val Ile Ala Asn Gly
                1025                1030                1035

Glu Ile Ile Phe Lys Leu Asp Gly Asp Ile Asp Arg Thr Gln Phe
                1040                1045                1050

Ile Trp Met Lys Tyr Phe Ser Ile Phe Asn Thr Glu Leu Ser Gln
                1055                1060                1065

Ser Asn Ile Glu Glu Arg Tyr Lys Ile Gln Ser Tyr Ser Glu Tyr
                1070                1075                1080

Leu Lys Asp Phe Trp Gly Asn Pro Leu Met Tyr Asn Lys Glu Tyr
                1085                1090                1095

Tyr Met Phe Asn Ala Gly Asn Lys Asn Ser Tyr Ile Lys Leu Lys
                1100                1105                1110

Lys Asp Ser Pro Val Gly Glu Ile Leu Thr Arg Ser Lys Tyr Asn
                1115                1120                1125

Gln Asn Ser Lys Tyr Ile Asn Tyr Arg Asp Leu Tyr Ile Gly Glu
                1130                1135                1140
```

-continued

```
Lys Phe Ile Ile Arg Arg Lys Ser Asn Ser Gln Ser Ile Asn Asp
    1145            1150                1155

Asp Ile Val Arg Lys Glu Asp Tyr Ile Tyr Leu Asp Phe Phe Asn
    1160            1165                1170

Leu Asn Gln Glu Trp Arg Val Tyr Thr Tyr Lys Tyr Phe Lys Lys
    1175            1180                1185

Glu Glu Glu Lys Leu Phe Leu Ala Pro Ile Ser Asp Ser Asp Glu
    1190            1195                1200

Phe Tyr Asn Thr Ile Gln Ile Lys Glu Tyr Asp Glu Gln Pro Thr
    1205            1210                1215

Tyr Ser Cys Gln Leu Leu Phe Lys Lys Asp Glu Glu Ser Thr Asp
    1220            1225                1230

Glu Ile Gly Leu Ile Gly Ile His Arg Phe Tyr Glu Ser Gly Ile
    1235            1240                1245

Val Phe Glu Glu Tyr Lys Asp Tyr Phe Cys Ile Ser Lys Trp Tyr
    1250            1255                1260

Leu Lys Glu Val Lys Arg Lys Pro Tyr Asn Leu Lys Leu Gly Cys
    1265            1270                1275

Asn Trp Gln Phe Ile Pro Lys Asp Glu Gly Trp Thr Glu
    1280            1285                1290

<210> SEQ ID NO 19
<211> LENGTH: 1280
<212> TYPE: PRT
<213> ORGANISM: Clostridium botulinum

<400> SEQUENCE: 19

Met Pro Ile Thr Ile Asn Asn Phe Asn Tyr Ser Asp Pro Val Asp Asn
1               5                   10                  15

Lys Asn Ile Leu Tyr Leu Asp Thr His Leu Asn Thr Leu Ala Asn Glu
                20                  25                  30

Pro Glu Lys Ala Phe Arg Ile Ile Gly Asn Ile Trp Val Ile Pro Asp
            35                  40                  45

Arg Phe Ser Arg Asp Ser Asn Pro Asn Leu Asn Lys Pro Pro Arg Val
    50                  55                  60

Thr Ser Pro Lys Ser Gly Tyr Tyr Asp Pro Asn Tyr Leu Ser Thr Asp
65                  70                  75                  80

Ser Glu Lys Asp Thr Phe Leu Lys Glu Ile Ile Lys Leu Phe Lys Arg
                85                  90                  95

Ile Asn Ser Arg Glu Ile Gly Glu Glu Leu Ile Tyr Arg Leu Ala Thr
                100                 105                 110

Asp Ile Pro Phe Pro Gly Asn Asn Asn Thr Pro Ile Asn Thr Phe Asp
            115                 120                 125

Phe Asp Val Asp Phe Asn Ser Val Asp Val Lys Thr Arg Gln Gly Asn
    130                 135                 140

Asn Trp Val Lys Thr Gly Ser Ile Asn Pro Ser Val Ile Ile Thr Gly
145                 150                 155                 160

Pro Arg Glu Asn Ile Ile Asp Pro Glu Thr Ser Thr Phe Lys Leu Thr
                165                 170                 175

Asn Asn Thr Phe Ala Ala Gln Glu Gly Phe Gly Ala Leu Ser Ile Ile
                180                 185                 190

Ser Ile Ser Pro Arg Phe Met Leu Thr Tyr Ser Asn Ala Thr Asn Asn
            195                 200                 205

Val Gly Glu Gly Arg Phe Ser Lys Ser Glu Phe Cys Met Asp Pro Ile
    210                 215                 220
```

```
Leu Ile Leu Met His Glu Leu Asn His Ala Met His Asn Leu Tyr Gly
225                 230                 235                 240

Ile Ala Ile Pro Asn Asp Gln Arg Ile Ser Ser Val Thr Ser Asn Ile
            245                 250                 255

Phe Tyr Ser Gln Tyr Lys Val Lys Leu Glu Tyr Ala Glu Ile Tyr Ala
        260                 265                 270

Phe Gly Gly Pro Thr Ile Asp Leu Ile Pro Lys Ser Ala Arg Lys Tyr
        275                 280                 285

Phe Glu Glu Lys Ala Leu Asp Tyr Tyr Arg Ser Ile Ala Lys Arg Leu
    290                 295                 300

Asn Ser Ile Thr Thr Ala Asn Pro Ser Ser Phe Asn Lys Tyr Ile Gly
305                 310                 315                 320

Glu Tyr Lys Gln Lys Leu Ile Arg Lys Tyr Arg Phe Val Val Glu Ser
                325                 330                 335

Ser Gly Glu Val Ala Val Asp Arg Asn Lys Phe Ala Glu Leu Tyr Lys
            340                 345                 350

Glu Leu Thr Gln Ile Phe Thr Glu Phe Asn Tyr Ala Lys Ile Tyr Asn
        355                 360                 365

Val Gln Asn Arg Lys Ile Tyr Leu Ser Asn Val Tyr Thr Pro Val Thr
    370                 375                 380

Ala Asn Ile Leu Asp Asp Asn Val Tyr Asp Ile Gln Asn Gly Phe Asn
385                 390                 395                 400

Ile Pro Lys Ser Asn Leu Asn Val Leu Phe Met Gly Gln Asn Leu Ser
                405                 410                 415

Arg Asn Pro Ala Leu Arg Lys Val Asn Pro Glu Asn Met Leu Tyr Leu
            420                 425                 430

Phe Thr Lys Phe Cys His Lys Ala Ile Asp Gly Arg Ser Leu Tyr Asn
        435                 440                 445

Lys Thr Leu Asp Cys Arg Glu Leu Leu Val Lys Asn Thr Asp Leu Pro
    450                 455                 460

Phe Ile Gly Asp Ile Ser Asp Ile Lys Thr Asp Ile Phe Leu Ser Lys
465                 470                 475                 480

Asp Ile Asn Glu Glu Thr Glu Val Ile Asp Tyr Pro Asp Asn Val Ser
                485                 490                 495

Val Asp Gln Val Ile Leu Ser Lys Asn Thr Ser Glu His Gly Gln Leu
            500                 505                 510

Asp Leu Leu Tyr Pro Ile Ile Glu Gly Glu Ser Gln Val Leu Pro Gly
        515                 520                 525

Glu Asn Gln Val Phe Tyr Asp Asn Arg Thr Gln Asn Val Asp Tyr Leu
    530                 535                 540

Asn Ser Tyr Tyr Tyr Leu Glu Ser Gln Lys Leu Ser Asp Asn Val Glu
545                 550                 555                 560

Asp Phe Thr Phe Thr Thr Ser Ile Glu Glu Ala Leu Asp Asn Ser Gly
                565                 570                 575

Lys Val Tyr Thr Tyr Phe Pro Lys Leu Ala Asp Lys Val Asn Thr Gly
            580                 585                 590

Val Gln Gly Gly Leu Phe Leu Met Trp Ala Asn Asp Val Val Glu Asp
        595                 600                 605

Phe Thr Thr Asn Ile Leu Arg Lys Asp Thr Leu Asp Lys Ile Ser Asp
    610                 615                 620

Val Ser Ala Ile Ile Pro Tyr Ile Gly Pro Ala Leu Asn Ile Ser Asn
625                 630                 635                 640

Ser Val Arg Arg Gly Asn Phe Thr Glu Ala Phe Ala Val Thr Gly Val
```

```
                    645                 650                 655
Thr Ile Leu Leu Glu Ala Phe Gln Glu Phe Thr Ile Pro Ala Leu Gly
            660                 665                 670

Ala Phe Val Ile Tyr Ser Lys Val Gln Glu Arg Asn Glu Ile Ile Lys
            675                 680                 685

Thr Ile Asp Asn Cys Leu Glu Gln Arg Ile Lys Arg Trp Lys Asp Ser
            690                 695                 700

Tyr Glu Trp Met Ile Gly Thr Trp Leu Ser Arg Ile Thr Thr Gln Phe
705                 710                 715                 720

Asn Asn Ile Ser Tyr Gln Met Tyr Asp Ser Leu Asn Tyr Gln Ala Asp
                725                 730                 735

Ala Ile Lys Asp Lys Ile Asp Leu Glu Tyr Lys Tyr Ser Gly Ser
            740                 745                 750

Asp Lys Glu Asn Ile Lys Ser Gln Val Glu Asn Leu Lys Asn Ser Leu
            755                 760                 765

Asp Ile Lys Ile Ser Glu Ala Met Asn Ile Asn Lys Phe Ile Arg
            770                 775                 780

Glu Cys Ser Val Thr Tyr Leu Phe Lys Asn Met Leu Pro Lys Val Ile
785                 790                 795                 800

Asp Glu Leu Asn Lys Phe Asp Leu Lys Thr Lys Thr Glu Leu Ile Asn
                805                 810                 815

Leu Ile Asp Ser His Asn Ile Ile Leu Val Gly Glu Val Asp Arg Leu
            820                 825                 830

Lys Ala Lys Val Asn Glu Ser Phe Glu Asn Thr Ile Pro Phe Asn Ile
            835                 840                 845

Phe Ser Tyr Thr Asn Asn Ser Leu Leu Lys Asp Ile Ile Asn Glu Tyr
            850                 855                 860

Phe Asn Ser Ile Asn Asp Ser Lys Ile Leu Ser Leu Gln Asn Lys Lys
865                 870                 875                 880

Asn Ala Leu Val Asp Thr Ser Gly Tyr Asn Ala Glu Val Arg Leu Glu
                885                 890                 895

Gly Asp Val Gln Val Asn Thr Ile Tyr Thr Asn Asp Phe Lys Leu Ser
            900                 905                 910

Ser Ser Gly Asp Lys Ile Ile Val Asn Leu Asn Asn Ile Leu Tyr
            915                 920                 925

Ser Ala Ile Tyr Glu Asn Ser Ser Val Ser Phe Trp Ile Lys Ile Ser
            930                 935                 940

Lys Asp Leu Thr Asn Ser His Asn Glu Tyr Thr Ile Ile Asn Ser Ile
945                 950                 955                 960

Lys Gln Asn Ser Gly Trp Lys Leu Cys Ile Arg Asn Gly Asn Ile Glu
                965                 970                 975

Trp Ile Leu Gln Asp Ile Asn Arg Lys Tyr Lys Ser Leu Ile Phe Asp
            980                 985                 990

Tyr Ser Glu Ser Leu Ser His Thr Gly Tyr Thr Asn Lys Trp Phe Phe
            995                 1000                1005

Val Thr Ile Thr Asn Asn Ile Met Gly Tyr Met Lys Leu Tyr Ile
            1010                1015                1020

Asn Gly Glu Leu Lys Gln Ser Glu Arg Ile Glu Asp Leu Asn Glu
            1025                1030                1035

Val Lys Leu Asp Lys Thr Ile Val Phe Gly Ile Asp Glu Asn Ile
            1040                1045                1050

Asp Glu Asn Gln Met Leu Trp Ile Arg Asp Phe Asn Ile Phe Ser
            1055                1060                1065
```

```
Lys Glu  Leu Ser Asn Glu  Asp Ile Asn Ile  Val Tyr Glu Gly  Gln
    1070             1075             1080

Ile Leu  Arg Asn Val Ile  Lys Asp Tyr Trp  Gly Asn Pro Leu  Lys
    1085             1090             1095

Phe Asp  Thr Glu Tyr Tyr  Ile Ile Asn Asp  Asn Tyr Ile Asp  Arg
    1100             1105             1110

Tyr Ile  Ala Pro Lys Ser  Asn Ile Leu Val  Leu Val Gln Tyr  Pro
    1115             1120             1125

Asp Arg  Ser Lys Leu Tyr  Thr Gly Asn Pro  Ile Thr Ile Lys  Ser
    1130             1135             1140

Val Ser  Asp Lys Asn Pro  Tyr Ser Arg Ile  Leu Asn Gly Asp  Asn
    1145             1150             1155

Ile Met  Phe His Met Leu  Tyr Asn Ser Gly  Lys Tyr Met Ile  Ile
    1160             1165             1170

Arg Asp  Thr Asp Thr Ile  Tyr Ala Ile Glu  Gly Arg Glu Cys  Ser
    1175             1180             1185

Lys Asn  Cys Val Tyr Ala  Leu Lys Leu Gln  Ser Asn Leu Gly  Asn
    1190             1195             1200

Tyr Gly  Ile Gly Ile Phe  Ser Ile Lys Asn  Ile Val Ser Gln  Asn
    1205             1210             1215

Lys Tyr  Cys Ser Gln Ile  Phe Ser Ser Phe  Met Lys Asn Thr  Met
    1220             1225             1230

Leu Leu  Ala Asp Ile Tyr  Lys Pro Trp Arg  Phe Ser Phe Glu  Asn
    1235             1240             1245

Ala Tyr  Thr Pro Val Ala  Val Thr Asn Tyr  Glu Thr Lys Leu  Leu
    1250             1255             1260

Ser Thr  Ser Ser Phe Trp  Lys Phe Ile Ser  Arg Asp Pro Gly  Trp
    1265             1270             1275

Val Glu
    1280

<210> SEQ ID NO 20
<211> LENGTH: 1285
<212> TYPE: PRT
<213> ORGANISM: Clostridium botulinum

<400> SEQUENCE: 20

Met Thr Trp Pro Val Lys Asp Phe Asn Tyr Ser Asp Pro Val Asn Asp
1               5                   10                  15

Asn Asp Ile Leu Tyr Leu Arg Ile Pro Gln Asn Lys Leu Ile Thr Thr
            20                  25                  30

Pro Val Lys Ala Phe Met Ile Thr Gln Asn Ile Trp Val Ile Pro Glu
        35                  40                  45

Arg Phe Ser Ser Asp Thr Asn Pro Ser Leu Ser Lys Pro Pro Arg Pro
    50                  55                  60

Thr Ser Lys Tyr Gln Ser Tyr Tyr Asp Pro Ser Tyr Leu Ser Thr Asp
65                  70                  75                  80

Glu Gln Lys Asp Thr Phe Leu Lys Gly Ile Ile Lys Leu Phe Lys Arg
                85                  90                  95

Ile Asn Glu Arg Asp Ile Gly Lys Lys Leu Ile Asn Tyr Leu Val Val
            100                 105                 110

Gly Ser Pro Phe Met Gly Asp Ser Ser Thr Pro Glu Asp Thr Phe Asp
        115                 120                 125

Phe Thr Arg His Thr Thr Asn Ile Ala Val Glu Lys Phe Glu Asn Gly
    130                 135                 140
```

```
Ser Trp Lys Val Thr Asn Ile Ile Thr Pro Ser Val Leu Ile Phe Gly
145                 150                 155                 160

Pro Leu Pro Asn Ile Leu Asp Tyr Thr Ala Ser Leu Thr Leu Gln Gly
            165                 170                 175

Gln Gln Ser Asn Pro Ser Phe Glu Gly Phe Gly Thr Leu Ser Ile Leu
            180                 185                 190

Lys Val Ala Pro Glu Phe Leu Leu Thr Phe Ser Asp Val Thr Ser Asn
        195                 200                 205

Gln Ser Ser Ala Val Leu Gly Lys Ser Ile Phe Cys Met Asp Pro Val
        210                 215                 220

Ile Ala Leu Met His Glu Leu Thr His Ser Leu His Gln Leu Tyr Gly
225                 230                 235                 240

Ile Asn Ile Pro Ser Asp Lys Arg Ile Arg Pro Gln Val Ser Glu Gly
                245                 250                 255

Phe Phe Ser Gln Asp Gly Pro Asn Val Gln Phe Glu Glu Leu Tyr Thr
            260                 265                 270

Phe Gly Gly Ser Asp Val Glu Ile Ile Pro Gln Ile Glu Arg Leu Gln
            275                 280                 285

Leu Arg Glu Lys Ala Leu Gly His Tyr Lys Asp Ile Ala Lys Arg Leu
290                 295                 300

Asn Asn Ile Asn Lys Thr Ile Pro Ser Ser Trp Ser Ser Asn Ile Asp
305                 310                 315                 320

Lys Tyr Lys Lys Ile Phe Ser Glu Lys Tyr Asn Phe Asp Lys Asp Asn
                325                 330                 335

Thr Gly Asn Phe Val Val Asn Ile Asp Lys Phe Asn Ser Leu Tyr Ser
            340                 345                 350

Asp Leu Thr Asn Val Met Ser Glu Val Val Tyr Ser Ser Gln Tyr Asn
        355                 360                 365

Val Lys Asn Arg Thr His Tyr Phe Ser Lys His Tyr Leu Pro Val Phe
370                 375                 380

Ala Asn Ile Leu Asp Asp Asn Ile Tyr Thr Ile Ile Asn Gly Phe Asn
385                 390                 395                 400

Leu Thr Thr Lys Gly Phe Asn Ile Glu Asn Ser Gly Gln Asn Ile Glu
                405                 410                 415

Arg Asn Pro Ala Leu Gln Lys Leu Ser Ser Glu Ser Val Val Asp Leu
            420                 425                 430

Phe Thr Lys Val Cys Leu Arg Leu Thr Arg Asn Ser Arg Asp Asp Ser
        435                 440                 445

Thr Cys Ile Gln Val Lys Asn Asn Thr Leu Pro Tyr Val Ala Asp Lys
        450                 455                 460

Asp Ser Ile Ser Gln Glu Ile Phe Glu Ser Gln Ile Ile Thr Asp Glu
465                 470                 475                 480

Thr Asn Val Glu Asn Tyr Ser Asp Asn Phe Ser Leu Asp Ser Ile
                485                 490                 495

Leu Asp Ala Lys Val Pro Thr Asn Pro Glu Ala Val Asp Pro Leu Leu
            500                 505                 510

Pro Asn Val Asn Met Glu Pro Leu Asn Val Pro Gly Glu Glu Val
            515                 520                 525

Phe Tyr Asp Asp Ile Thr Lys Asp Val Asp Tyr Leu Asn Ser Tyr Tyr
530                 535                 540

Tyr Leu Glu Ala Gln Lys Leu Ser Asn Asn Val Glu Asn Ile Thr Leu
545                 550                 555                 560

Thr Thr Ser Val Glu Glu Ala Leu Gly Tyr Ser Asn Lys Ile Tyr Thr
                565                 570                 575
```

-continued

Phe Leu Pro Ser Leu Ala Glu Lys Val Asn Lys Gly Val Gln Ala Gly
            580                 585                 590

Leu Phe Leu Asn Trp Ala Asn Glu Val Val Glu Asp Phe Thr Thr Asn
        595                 600                 605

Ile Met Lys Lys Asp Thr Leu Asp Lys Ile Ser Asp Val Ser Ala Ile
610                 615                 620

Ile Pro Tyr Ile Gly Pro Ala Leu Asn Ile Gly Asn Ser Ala Leu Arg
625                 630                 635                 640

Gly Asn Phe Lys Gln Ala Phe Ala Thr Ala Gly Val Ala Phe Leu Leu
                645                 650                 655

Glu Gly Phe Pro Glu Phe Thr Ile Pro Ala Leu Gly Val Phe Thr Phe
            660                 665                 670

Tyr Ser Ser Ile Gln Glu Arg Glu Lys Ile Ile Lys Thr Ile Glu Asn
            675                 680                 685

Cys Leu Glu Gln Arg Val Lys Arg Trp Lys Asp Ser Tyr Gln Trp Met
    690                 695                 700

Val Ser Asn Trp Leu Ser Arg Ile Thr Thr Arg Phe Asn His Ile Ser
705                 710                 715                 720

Tyr Gln Met Tyr Asp Ser Leu Ser Tyr Gln Ala Asp Ala Ile Lys Ala
                725                 730                 735

Lys Ile Asp Leu Glu Tyr Lys Lys Tyr Ser Gly Ser Asp Lys Glu Asn
                740                 745                 750

Ile Lys Ser Gln Val Glu Asn Leu Lys Asn Ser Leu Asp Val Lys Ile
            755                 760                 765

Ser Glu Ala Met Asn Asn Ile Asn Lys Phe Ile Arg Glu Cys Ser Val
    770                 775                 780

Thr Tyr Leu Phe Lys Asn Met Leu Pro Lys Val Ile Asp Glu Leu Asn
785                 790                 795                 800

Lys Phe Asp Leu Lys Thr Lys Thr Glu Leu Ile Asn Leu Ile Asp Ser
                805                 810                 815

His Asn Ile Ile Leu Val Gly Glu Val Asp Arg Leu Lys Ala Lys Val
            820                 825                 830

Asn Glu Ser Phe Glu Asn Thr Ile Pro Phe Asn Ile Phe Ser Tyr Thr
    835                 840                 845

Asn Asn Ser Leu Leu Lys Asp Met Ile Asn Glu Tyr Phe Asn Ser Ile
850                 855                 860

Asn Asp Ser Lys Ile Leu Ser Leu Gln Asn Lys Lys Asn Thr Leu Met
865                 870                 875                 880

Asp Thr Ser Gly Tyr Asn Ala Glu Val Arg Val Glu Gly Asn Val Gln
                885                 890                 895

Leu Asn Pro Ile Phe Pro Phe Asp Phe Lys Leu Gly Ser Ser Gly Asp
            900                 905                 910

Asp Arg Gly Lys Val Ile Val Thr Gln Asn Glu Asn Ile Val Tyr Asn
            915                 920                 925

Ala Met Tyr Glu Ser Phe Ser Ile Ser Phe Trp Ile Arg Ile Asn Lys
    930                 935                 940

Trp Val Ser Asn Leu Pro Gly Tyr Thr Ile Ile Asp Ser Val Lys Asn
945                 950                 955                 960

Asn Ser Gly Trp Ser Ile Gly Ile Ile Ser Asn Phe Leu Val Phe Thr
                965                 970                 975

Leu Lys Gln Asn Glu Asn Ser Glu Gln Asp Ile Asn Phe Ser Tyr Asp
            980                 985                 990

Ile Ser Lys Asn Ala Ala Gly Tyr  Asn Lys Trp Phe Phe  Val Thr Ile

-continued

```
                995                 1000                1005
    Thr Thr Asn Met Met Gly Asn Met Met Ile Tyr Ile Asn Gly Lys
        1010                1015                1020

Leu Ile Asp Thr Ile Lys Val Lys Glu Leu Thr Gly Ile Asn Phe
        1025                1030                1035

Ser Lys Thr Ile Thr Phe Gln Met Asn Lys Ile Pro Asn Thr Gly
        1040                1045                1050

Leu Ile Thr Ser Asp Ser Asp Asn Ile Asn Met Trp Ile Arg Asp
        1055                1060                1065

Phe Tyr Ile Phe Ala Lys Glu Leu Asp Asp Lys Asp Ile Asn Ile
        1070                1075                1080

Leu Phe Asn Ser Leu Gln Tyr Thr Asn Val Val Lys Asp Tyr Trp
        1085                1090                1095

Gly Asn Asp Leu Arg Tyr Asp Lys Glu Tyr Tyr Met Ile Asn Val
        1100                1105                1110

Asn Tyr Met Asn Arg Tyr Met Ser Lys Lys Gly Asn Gly Ile Val
        1115                1120                1125

Phe Asn Thr Arg Lys Asn Asn Asn Asp Phe Asn Glu Gly Tyr Lys
        1130                1135                1140

Ile Ile Ile Lys Arg Ile Arg Gly Asn Thr Asn Asp Thr Arg Val
        1145                1150                1155

Arg Gly Glu Asn Val Leu Tyr Phe Asn Thr Thr Ile Asp Asn Lys
        1160                1165                1170

Gln Tyr Ser Leu Gly Met Tyr Lys Pro Ser Arg Asn Leu Gly Thr
        1175                1180                1185

Asp Leu Val Pro Leu Gly Ala Leu Asp Gln Pro Met Asp Glu Ile
        1190                1195                1200

Arg Lys Tyr Gly Ser Phe Ile Ile Gln Pro Cys Asn Thr Phe Asp
        1205                1210                1215

Tyr Tyr Ala Ser Gln Leu Phe Leu Ser Ser Asn Ala Thr Thr Asn
        1220                1225                1230

Arg Leu Gly Ile Leu Ser Ile Gly Ser Tyr Ser Phe Lys Leu Gly
        1235                1240                1245

Asp Asp Tyr Trp Phe Asn His Glu Tyr Leu Ile Pro Val Ile Lys
        1250                1255                1260

Ile Glu His Tyr Ala Ser Leu Leu Glu Ser Thr Ser Thr His Trp
        1265                1270                1275

Val Phe Val Pro Ala Ser Glu
        1280                1285

<210> SEQ ID NO 21
<211> LENGTH: 1251
<212> TYPE: PRT
<213> ORGANISM: Clostridium botulinum

<400> SEQUENCE: 21

Met Pro Lys Ile Asn Ser Phe Asn Tyr Asn Asp Pro Val Asn Asp Arg
1               5                   10                  15

Thr Ile Leu Tyr Ile Lys Pro Gly Gly Cys Gln Glu Phe Tyr Lys Ser
                20                  25                  30

Phe Asn Ile Met Lys Asn Ile Trp Ile Ile Pro Glu Arg Asn Val Ile
            35                  40                  45

Gly Thr Thr Pro Gln Asp Phe His Pro Pro Thr Ser Leu Lys Asn Gly
        50                  55                  60

Asp Ser Ser Tyr Tyr Asp Pro Asn Tyr Leu Gln Ser Asp Glu Glu Lys
```

-continued

```
            65                  70                  75                  80
Asp Arg Phe Leu Lys Ile Val Thr Lys Ile Phe Asn Arg Ile Asn Asn
                    85                  90                  95
Asn Leu Ser Gly Gly Ile Leu Leu Glu Glu Leu Ser Lys Ala Asn Pro
                    100                 105                 110
Tyr Leu Gly Asn Asp Asn Thr Pro Asp Asn Gln Phe His Ile Gly Asp
                    115                 120                 125
Ala Ser Ala Val Glu Ile Lys Phe Ser Asn Gly Ser Gln Asp Ile Leu
                    130                 135                 140
Leu Pro Asn Val Ile Ile Met Gly Ala Glu Pro Asp Leu Phe Glu Thr
145                 150                 155                 160
Asn Ser Ser Asn Ile Ser Leu Arg Asn Asn Tyr Met Pro Ser Asn His
                    165                 170                 175
Arg Phe Gly Ser Ile Ala Ile Val Thr Phe Ser Pro Glu Tyr Ser Phe
                    180                 185                 190
Arg Phe Asn Asp Asn Cys Met Asn Glu Phe Ile Gln Asp Pro Ala Leu
                    195                 200                 205
Thr Leu Met His Glu Leu Ile His Ser Leu His Gly Leu Tyr Gly Ala
                    210                 215                 220
Lys Gly Ile Thr Thr Lys Tyr Thr Ile Thr Gln Lys Gln Asn Pro Leu
225                 230                 235                 240
Ile Thr Asn Ile Arg Gly Thr Asn Ile Glu Glu Phe Leu Thr Phe Gly
                    245                 250                 255
Gly Thr Asp Leu Asn Ile Ile Thr Ser Ala Gln Ser Asn Asp Ile Tyr
                    260                 265                 270
Thr Asn Leu Leu Ala Asp Tyr Lys Lys Ile Ala Ser Lys Leu Ser Lys
                    275                 280                 285
Val Gln Val Ser Asn Pro Leu Leu Asn Pro Tyr Lys Asp Val Phe Glu
290                 295                 300
Ala Lys Tyr Gly Leu Asp Lys Asp Ala Ser Gly Ile Tyr Ser Val Asn
305                 310                 315                 320
Ile Asn Lys Phe Asn Asp Ile Phe Lys Lys Leu Tyr Ser Phe Thr Glu
                    325                 330                 335
Phe Asp Leu Arg Thr Lys Phe Gln Val Lys Cys Arg Gln Thr Tyr Ile
                    340                 345                 350
Gly Gln Tyr Lys Tyr Phe Lys Leu Ser Asn Leu Leu Asn Asp Ser Ile
                    355                 360                 365
Tyr Asn Ile Ser Glu Gly Tyr Asn Ile Asn Asn Leu Lys Val Asn Phe
                    370                 375                 380
Arg Gly Gln Asn Ala Asn Leu Asn Pro Arg Ile Ile Thr Pro Ile Thr
385                 390                 395                 400
Gly Arg Gly Leu Val Lys Lys Ile Ile Arg Phe Cys Lys Asn Ile Val
                    405                 410                 415
Ser Val Lys Gly Ile Arg Lys Ser Ile Cys Ile Glu Ile Asn Asn Gly
                    420                 425                 430
Glu Leu Phe Phe Val Ala Ser Glu Asn Ser Tyr Asn Asp Asp Asn Ile
                    435                 440                 445
Asn Thr Pro Lys Glu Ile Asp Asp Thr Val Thr Ser Asn Asn Asn Tyr
                    450                 455                 460
Glu Asn Asp Leu Asp Gln Val Ile Leu Asn Phe Asn Ser Glu Ser Ala
465                 470                 475                 480
Pro Gly Leu Ser Asp Glu Lys Leu Asn Leu Thr Ile Gln Asn Asp Ala
                    485                 490                 495
```

```
Tyr Ile Pro Lys Tyr Asp Ser Asn Gly Thr Ser Asp Ile Glu Gln His
            500                 505                 510

Asp Val Asn Glu Leu Asn Val Phe Tyr Leu Asp Ala Gln Lys Val
        515                 520                 525

Pro Glu Gly Glu Asn Asn Val Asn Leu Thr Ser Ser Ile Asp Thr Ala
        530                 535                 540

Leu Leu Glu Gln Pro Lys Ile Tyr Thr Phe Phe Ser Ser Glu Phe Ile
545                 550                 555                 560

Asn Asn Val Asn Lys Pro Val Gln Ala Ala Leu Phe Val Ser Trp Ile
                565                 570                 575

Gln Gln Val Leu Val Asp Phe Thr Thr Glu Ala Asn Gln Lys Ser Thr
            580                 585                 590

Val Asp Lys Ile Ala Asp Ile Ser Ile Val Val Pro Tyr Ile Gly Leu
        595                 600                 605

Ala Leu Asn Ile Gly Asn Glu Ala Gln Lys Gly Asn Phe Lys Asp Ala
        610                 615                 620

Leu Glu Leu Leu Gly Ala Gly Ile Leu Leu Glu Phe Glu Pro Glu Leu
625                 630                 635                 640

Leu Ile Pro Thr Ile Leu Val Phe Thr Ile Lys Ser Phe Leu Gly Ser
                645                 650                 655

Ser Asp Asn Lys Asn Lys Val Ile Lys Ala Ile Asn Asn Ala Leu Lys
            660                 665                 670

Glu Arg Asp Glu Lys Trp Lys Glu Val Tyr Ser Phe Ile Val Ser Asn
        675                 680                 685

Trp Met Thr Lys Ile Asn Thr Gln Phe Asn Lys Arg Lys Glu Gln Met
690                 695                 700

Tyr Gln Ala Leu Gln Asn Gln Val Asn Ala Ile Lys Thr Ile Ile Glu
705                 710                 715                 720

Ser Lys Tyr Asn Ser Tyr Thr Leu Glu Glu Lys Asn Glu Leu Thr Asn
                725                 730                 735

Lys Tyr Asp Ile Lys Gln Ile Glu Asn Glu Leu Asn Gln Lys Val Ser
            740                 745                 750

Ile Ala Met Asn Asn Ile Asp Arg Phe Leu Thr Glu Ser Ser Ile Ser
        755                 760                 765

Tyr Leu Met Lys Ile Ile Asn Glu Val Lys Ile Asn Lys Leu Arg Glu
        770                 775                 780

Tyr Asp Glu Asn Val Lys Thr Tyr Leu Leu Asn Tyr Ile Ile Gln His
785                 790                 795                 800

Gly Ser Ile Leu Gly Glu Ser Gln Gln Glu Leu Asn Ser Met Val Thr
                805                 810                 815

Asp Thr Leu Asn Asn Ser Ile Pro Phe Lys Leu Ser Ser Tyr Thr Asp
            820                 825                 830

Asp Lys Ile Leu Ile Ser Tyr Phe Asn Lys Phe Phe Lys Arg Ile Lys
        835                 840                 845

Ser Ser Ser Val Leu Asn Met Arg Tyr Lys Asn Asp Lys Tyr Val Asp
        850                 855                 860

Thr Ser Gly Tyr Asp Ser Asn Ile Asn Ile Asn Gly Asp Val Tyr Lys
865                 870                 875                 880

Tyr Pro Thr Asn Lys Asn Gln Phe Gly Ile Tyr Asn Asp Lys Leu Ser
                885                 890                 895

Glu Val Asn Ile Ser Gln Asn Asp Tyr Ile Ile Tyr Asp Asn Lys Tyr
            900                 905                 910

Lys Asn Phe Ser Ile Ser Phe Trp Val Arg Ile Pro Asn Tyr Asp Asn
        915                 920                 925
```

```
Lys Ile Val Asn Val Asn Asn Glu Tyr Thr Ile Ile Asn Cys Met Arg
            930                 935                 940

Asp Asn Asn Ser Gly Trp Lys Val Ser Leu Asn His Asn Glu Ile Ile
945                 950                 955                 960

Trp Thr Phe Glu Asp Asn Arg Gly Ile Asn Gln Lys Leu Ala Phe Asn
                965                 970                 975

Tyr Gly Asn Ala Asn Gly Ile Ser Asp Tyr Ile Asn Lys Trp Ile Phe
            980                 985                 990

Val Thr Ile Thr Asn Asp Arg Leu Gly Asp Ser Lys Leu Tyr Ile Asn
        995                1000               1005

Gly Asn Leu Ile Asp Gln Lys Ser Ile Leu Asn Leu Gly Asn Ile
       1010                1015               1020

His Val Ser Asp Asn Ile Leu Phe Lys Ile Val Asn Cys Ser Tyr
       1025                1030               1035

Thr Arg Tyr Ile Gly Ile Arg Tyr Phe Asn Ile Phe Asp Lys Glu
       1040                1045               1050

Leu Asp Glu Thr Glu Ile Gln Thr Leu Tyr Ser Asn Glu Pro Asn
       1055                1060               1065

Thr Asn Ile Leu Lys Asp Phe Trp Gly Asn Tyr Leu Leu Tyr Asp
       1070                1075               1080

Lys Glu Tyr Tyr Leu Leu Asn Val Leu Lys Pro Asn Asn Phe Ile
       1085                1090               1095

Asp Arg Arg Lys Asp Ser Thr Leu Ser Ile Asn Asn Ile Arg Ser
       1100                1105               1110

Thr Ile Leu Leu Ala Asn Arg Leu Tyr Ser Gly Ile Lys Val Lys
       1115                1120               1125

Ile Gln Arg Val Asn Asn Ser Ser Thr Asn Asp Asn Leu Val Arg
       1130                1135               1140

Lys Asn Asp Gln Val Tyr Ile Asn Phe Val Ala Ser Lys Thr His
       1145                1150               1155

Leu Phe Pro Leu Tyr Ala Asp Thr Ala Thr Thr Asn Lys Glu Lys
       1160                1165               1170

Thr Ile Lys Ile Ser Ser Ser Gly Asn Arg Phe Asn Gln Val Val
       1175                1180               1185

Val Met Asn Ser Val Gly Asn Cys Thr Met Asn Phe Lys Asn Asn
       1190                1195               1200

Asn Gly Asn Asn Ile Gly Leu Leu Gly Phe Lys Ala Asp Thr Val
       1205                1210               1215

Val Ala Ser Thr Trp Tyr Tyr Thr His Met Arg Asp His Thr Asn
       1220                1225               1230

Ser Asn Gly Cys Phe Trp Asn Phe Ile Ser Glu Glu His Gly Trp
       1235                1240               1245

Gln Glu Lys
       1250

<210> SEQ ID NO 22
<211> LENGTH: 1280
<212> TYPE: PRT
<213> ORGANISM: Clostridium botulinum

<400> SEQUENCE: 22

Met Pro Val Val Ile Asn Ser Phe Asn Tyr Asn Asp Pro Val Asn Asp
1               5                   10                  15

Glu Thr Ile Leu Tyr Met Gln Lys Pro Tyr Glu Glu Arg Ser Arg Lys
            20                  25                  30
```

```
Tyr Tyr Lys Ala Phe Glu Ile Met Pro Asn Val Trp Ile Met Pro Glu
         35                  40                  45

Arg Asp Thr Ile Gly Thr Lys Pro Asp Glu Phe Gln Val Pro Asp Ser
 50                  55                  60

Leu Lys Asn Gly Ser Ser Ala Tyr Tyr Asp Pro Asn Tyr Leu Thr Thr
 65                  70                  75                  80

Asp Ala Glu Lys Asp Arg Tyr Leu Lys Thr Met Ile Lys Leu Phe Asn
             85                  90                  95

Arg Ile Asn Ser Asn Pro Thr Gly Lys Val Leu Leu Glu Glu Val Ser
            100                 105                 110

Asn Ala Arg Pro Tyr Leu Gly Asp Asp Thr Leu Ile Asn Glu Phe
            115                 120                 125

Leu Pro Val Asn Val Thr Thr Ser Val Asn Ile Lys Phe Ser Thr Asp
        130                 135                 140

Val Glu Ser Ser Ile Ile Ser Asn Leu Leu Val Leu Gly Ala Gly Pro
145                 150                 155                 160

Asp Ile Phe Lys Ala Tyr Cys Thr Pro Leu Val Arg Phe Asn Lys Ser
                165                 170                 175

Asp Lys Leu Ile Glu Pro Ser Asn His Gly Phe Gly Ser Ile Asn Ile
            180                 185                 190

Leu Thr Phe Ser Pro Glu Tyr Glu His Ile Phe Asn Asp Ile Ser Gly
            195                 200                 205

Gly Asn His Asn Ser Thr Glu Ser Phe Ile Ala Asp Pro Ala Ile Ser
        210                 215                 220

Leu Ala His Glu Leu Ile His Ala Leu His Gly Leu Tyr Gly Ala Lys
225                 230                 235                 240

Ala Val Thr His Lys Glu Ser Leu Val Ala Glu Arg Gly Pro Leu Met
                245                 250                 255

Ile Ala Glu Lys Pro Ile Arg Leu Glu Glu Phe Leu Thr Phe Gly Gly
            260                 265                 270

Glu Asp Leu Asn Ile Ile Pro Ser Ala Met Lys Glu Lys Ile Tyr Asn
            275                 280                 285

Asp Leu Leu Ala Asn Tyr Glu Lys Ile Ala Thr Arg Leu Arg Glu Val
        290                 295                 300

Asn Thr Ala Pro Pro Gly Tyr Asp Ile Asn Glu Tyr Lys Asp Tyr Phe
305                 310                 315                 320

Gln Trp Lys Tyr Gly Leu Asp Arg Asn Ala Asp Gly Ser Tyr Thr Val
                325                 330                 335

Asn Arg Asn Lys Phe Asn Glu Ile Tyr Lys Lys Leu Tyr Ser Phe Thr
            340                 345                 350

Glu Ile Asp Leu Ala Asn Lys Phe Lys Val Lys Cys Arg Asn Thr Tyr
            355                 360                 365

Phe Ile Lys Tyr Gly Phe Val Lys Val Pro Asn Leu Leu Asp Asp Asp
370                 375                 380

Ile Tyr Thr Val Ser Glu Gly Phe Asn Ile Gly Asn Leu Ala Val Asn
385                 390                 395                 400

Asn Arg Gly Gln Asn Ile Asn Leu Asn Pro Lys Ile Ile Asp Ser Ile
                405                 410                 415

Pro Asp Lys Gly Leu Val Glu Lys Ile Ile Lys Phe Cys Lys Ser Ile
            420                 425                 430

Ile Pro Arg Lys Gly Thr Lys Gln Ser Pro Ser Leu Cys Ile Arg Val
            435                 440                 445

Asn Asn Arg Glu Leu Phe Phe Val Ala Ser Glu Ser Ser Tyr Asn Glu
```

```
               450                 455                 460
Ser Asp Ile Asn Thr Pro Lys Glu Ile Asp Thr Thr Asn Leu Asn
465                 470                 475                 480

Asn Asn Tyr Arg Asn Asn Leu Asp Glu Val Ile Leu Asp Tyr Asn Ser
                    485                 490                 495

Glu Thr Ile Pro Gln Ile Ser Asn Arg Thr Leu Asn Thr Leu Val Gln
                500                 505                 510

Asp Asn Ser Tyr Val Pro Arg Tyr Asp Ser Asn Gly Thr Ser Glu Ile
            515                 520                 525

Glu Glu Tyr Asp Val Val Asp Phe Asn Val Phe Phe Tyr Leu His Ala
        530                 535                 540

Gln Lys Val Pro Glu Gly Glu Thr Asn Ile Ser Leu Thr Ser Ser Ile
545                 550                 555                 560

Asp Thr Ala Leu Leu Glu Glu Ser Lys Val Tyr Thr Phe Phe Ser Ser
                565                 570                 575

Glu Phe Ile Asp Thr Ile Asn Lys Pro Val Asn Ala Ala Leu Phe Ile
                580                 585                 590

Asp Trp Ile Ser Lys Val Ile Arg Asp Phe Thr Thr Glu Ala Thr Gln
            595                 600                 605

Lys Ser Thr Val Asp Lys Ile Ala Asp Ile Ser Leu Ile Val Pro Tyr
        610                 615                 620

Val Gly Leu Ala Leu Asn Ile Val Ile Glu Ala Glu Lys Gly Asn Phe
625                 630                 635                 640

Glu Glu Ala Phe Glu Leu Leu Gly Ala Gly Ile Leu Leu Glu Phe Val
                645                 650                 655

Pro Glu Leu Thr Ile Pro Val Ile Leu Val Phe Thr Ile Lys Ser Tyr
                660                 665                 670

Ile Asp Ser Tyr Glu Asn Lys Asn Lys Ala Ile Lys Ala Ile Asn Asn
            675                 680                 685

Ser Leu Ile Glu Arg Glu Ala Lys Trp Lys Glu Ile Tyr Ser Trp Ile
        690                 695                 700

Val Ser Asn Trp Leu Thr Arg Ile Asn Thr Gln Phe Asn Lys Arg Lys
705                 710                 715                 720

Glu Gln Met Tyr Gln Ala Leu Gln Asn Gln Val Asp Ala Ile Lys Thr
                725                 730                 735

Ala Ile Glu Tyr Lys Tyr Asn Asn Tyr Thr Ser Asp Glu Lys Asn Arg
                740                 745                 750

Leu Glu Ser Lys Tyr Asn Ile Asn Asn Ile Glu Glu Glu Leu Asn Lys
            755                 760                 765

Lys Val Ser Leu Ala Met Lys Asn Ile Glu Arg Phe Met Thr Glu Ser
770                 775                 780

Ser Ile Ser Tyr Leu Met Lys Leu Ile Asn Glu Ala Glu Val Gly Lys
785                 790                 795                 800

Leu Lys Glu Tyr Asp Lys His Val Lys Ser Asp Leu Leu Asp Tyr Ile
                805                 810                 815

Leu Tyr His Lys Leu Ile Leu Gly Glu Gln Thr Lys Glu Leu Ile Asp
            820                 825                 830

Leu Val Thr Ser Thr Leu Asn Ser Ser Ile Pro Phe Glu Leu Ser Ser
        835                 840                 845

Tyr Thr Asn Asp Lys Ile Leu Ile Ile Tyr Phe Asn Arg Leu Tyr Lys
    850                 855                 860

Lys Ile Lys Asp Ser Ser Ile Leu Asp Met Arg Tyr Glu Asn Asn Lys
865                 870                 875                 880
```

-continued

```
Phe Ile Asp Ile Ser Gly Tyr Gly Ser Asn Ile Ser Ile Asn Gly Asn
            885                 890                 895

Val Tyr Ile Tyr Ser Thr Asn Arg Asn Gln Phe Gly Ile Tyr Ser Gly
        900                 905                 910

Arg Leu Ser Glu Val Asn Ile Ala Gln Asn Asn Asp Ile Ile Tyr Asn
        915                 920                 925

Ser Arg Tyr Gln Asn Phe Ser Ile Ser Phe Trp Val Thr Ile Pro Lys
    930                 935                 940

His Tyr Arg Pro Met Asn Arg Asn Arg Glu Tyr Thr Ile Ile Asn Cys
945                 950                 955                 960

Met Gly Asn Asn Asn Ser Gly Trp Lys Ile Ser Leu Arg Thr Ile Arg
                965                 970                 975

Asp Cys Glu Ile Ile Trp Thr Leu Gln Asp Thr Ser Gly Asn Lys Glu
                980                 985                 990

Lys Leu Ile Phe Arg Tyr Glu Glu  Leu Ala Ser Ile Ser  Asp Tyr Ile
            995                1000                 1005

Asn Lys  Trp Ile Phe Val Thr  Ile Thr Asn Asn Arg   Leu Gly Asn
   1010                1015                  1020

Ser Arg  Ile Tyr Ile Asn Gly  Asn Leu Ile Val Glu   Lys Ser Ile
   1025                1030                  1035

Ser Asn  Leu Gly Asp Ile His  Val Ser Asp Asn Ile   Leu Phe Lys
   1040                1045                  1050

Ile Val  Gly Cys Asp Asp Glu  Thr Tyr Val Gly Ile   Arg Tyr Phe
   1055                1060                  1065

Lys Val  Phe Asn Thr Glu Leu  Asp Lys Thr Glu Ile   Glu Thr Leu
   1070                1075                  1080

Tyr Ser  Asn Glu Pro Asp Pro  Ser Ile Leu Lys Asp   Tyr Trp Gly
   1085                1090                  1095

Asn Tyr  Leu Leu Tyr Asn Lys  Lys Tyr Tyr Leu Phe   Asn Leu Leu
   1100                1105                  1110

Arg Lys  Asp Lys Tyr Ile Thr  Arg Asn Ser Gly Ile   Leu Asn Ile
   1115                1120                  1125

Asn Gln  Gln Arg Gly Val Thr  Gly Gly Ile Ser Val   Phe Leu Asn
   1130                1135                  1140

Tyr Lys  Leu Tyr Glu Gly Val  Glu Val Ile Ile Arg   Lys Asn Ala
   1145                1150                  1155

Pro Ile  Asp Ile Ser Asn Thr  Asp Asn Phe Val Arg   Lys Asn Asp
   1160                1165                  1170

Leu Ala  Tyr Ile Asn Val Val  Asp His Gly Val Glu   Tyr Arg Leu
   1175                1180                  1185

Tyr Ala  Asp Ile Ser Ile Thr  Lys Ser Glu Lys Ile   Ile Lys Leu
   1190                1195                  1200

Ile Arg  Thr Ser Asn Pro Asn  Asp Ser Leu Gly Gln   Ile Ile Val
   1205                1210                  1215

Met Asp  Ser Ile Gly Asn Asn  Cys Thr Met Asn Phe   Gln Asn Asn
   1220                1225                  1230

Asp Gly  Ser Asn Ile Gly Leu  Leu Gly Phe His Ser   Asp Asp Leu
   1235                1240                  1245

Val Ala  Ser Ser Trp Tyr Tyr  Asn His Ile Arg Arg   Asn Thr Ser
   1250                1255                  1260

Ser Asn  Gly Cys Phe Trp Ser  Phe Ile Ser Lys Glu   His Gly Trp
   1265                1270                  1275

Lys Glu
   1280
```

```
<210> SEQ ID NO 23
<211> LENGTH: 1297
<212> TYPE: PRT
<213> ORGANISM: Clostridium botulinum
<220> FEATURE:
<221> NAME/KEY: misc_feature
<222> LOCATION: (7)..(7)
<223> OTHER INFORMATION: Xaa can be any naturally occurring amino acid

<400> SEQUENCE: 23
```

| | | | | | | | | | | | | | | |
|---|---|---|---|---|---|---|---|---|---|---|---|---|---|---|
|Met|Pro|Val|Asn|Ile|Lys|Xaa|Phe|Asn|Tyr|Asn|Asp|Pro|Ile|Asn|Asn|
|1| | | |5| | | | |10| | | | |15| |

| | | | | | | | | | | | | | |
|---|---|---|---|---|---|---|---|---|---|---|---|---|---|
|Asp|Asp|Ile|Ile|Met|Met|Glu|Pro|Phe|Asn|Asp|Gly|Pro|Gly|Thr|
| | | | |20| | | | |25| | | |30| |

Tyr Tyr Lys Ala Phe Arg Ile Ile Asp Arg Ile Trp Ile Val Pro Glu
              35                  40                  45

Arg Phe Thr Tyr Gly Phe Gln Pro Asp Gln Phe Asn Ala Ser Thr Gly
     50                  55                  60

Val Phe Ser Lys Asp Val Tyr Glu Tyr Tyr Asp Pro Thr Tyr Leu Lys
65                  70                  75                  80

Thr Asp Ala Glu Lys Asp Lys Phe Leu Lys Thr Met Ile Lys Leu Phe
                85                  90                  95

Asn Arg Ile Asn Ser Lys Pro Ser Gly Gln Arg Leu Leu Asp Met Ile
            100                 105                 110

Val Asp Ala Ile Pro Tyr Leu Gly Asn Ala Ser Thr Pro Pro Asp Lys
        115                 120                 125

Phe Ala Ala Asn Val Ala Asn Val Ser Ile Asn Lys Lys Ile Ile Gln
130                 135                 140

Pro Gly Ala Glu Asp Gln Ile Lys Gly Leu Met Thr Asn Leu Ile Ile
145                 150                 155                 160

Phe Gly Pro Gly Pro Val Leu Ser Asp Asn Phe Thr Asp Ser Met Ile
                165                 170                 175

Met Asn Gly His Ser Pro Ile Ser Glu Gly Phe Gly Ala Arg Met Met
            180                 185                 190

Ile Arg Phe Cys Pro Ser Cys Leu Asn Val Phe Asn Asn Val Gln Glu
        195                 200                 205

Asn Lys Asp Thr Ser Ile Phe Ser Arg Arg Ala Tyr Phe Ala Asp Pro
210                 215                 220

Ala Leu Thr Leu Met His Glu Leu Ile His Val Leu His Gly Leu Tyr
225                 230                 235                 240

Gly Ile Lys Ile Ser Asn Leu Pro Ile Thr Pro Asn Thr Lys Glu Phe
                245                 250                 255

Phe Met Gln His Ser Asp Pro Val Gln Ala Glu Glu Leu Tyr Thr Phe
            260                 265                 270

Gly Gly His Asp Pro Ser Val Ile Ser Pro Ser Thr Asp Met Asn Ile
        275                 280                 285

Tyr Asn Lys Ala Leu Gln Asn Phe Gln Asp Ile Ala Asn Arg Leu Asn
290                 295                 300

Ile Val Ser Ser Ala Gln Gly Ser Gly Ile Asp Ile Ser Leu Tyr Lys
305                 310                 315                 320

Gln Ile Tyr Lys Asn Lys Tyr Asp Phe Val Glu Asp Pro Asn Gly Lys
                325                 330                 335

Tyr Ser Val Asp Lys Asp Lys Phe Asp Lys Leu Tyr Lys Ala Leu Met
            340                 345                 350

Phe Gly Phe Thr Glu Thr Asn Leu Ala Gly Glu Tyr Gly Ile Lys Thr

```
                355                 360                 365
Arg Tyr Ser Tyr Phe Ser Glu Tyr Leu Pro Ile Lys Thr Glu Lys
    370                 375                 380
Leu Leu Asp Asn Thr Ile Tyr Thr Gln Asn Glu Gly Phe Asn Ile Ala
385                 390                 395                 400
Ser Lys Asn Leu Lys Thr Glu Phe Asn Gly Gln Asn Lys Ala Val Asn
                405                 410                 415
Lys Glu Ala Tyr Glu Glu Ile Ser Leu Glu His Leu Val Ile Tyr Arg
                420                 425                 430
Ile Ala Met Cys Lys Pro Val Met Tyr Lys Asn Thr Gly Lys Ser Glu
                435                 440                 445
Gln Cys Ile Ile Val Asn Asn Glu Asp Leu Phe Phe Ile Ala Asn Lys
                450                 455                 460
Asp Ser Phe Ser Lys Asp Leu Ala Lys Ala Glu Thr Ile Ala Tyr Asn
465                 470                 475                 480
Thr Gln Asn Asn Thr Ile Glu Asn Asn Phe Ser Ile Asp Gln Leu Ile
                485                 490                 495
Leu Asp Asn Asp Leu Ser Ser Gly Ile Asp Leu Pro Asn Glu Asn Thr
                500                 505                 510
Glu Pro Phe Thr Asn Phe Asp Asp Ile Asp Ile Pro Val Tyr Ile Lys
                515                 520                 525
Gln Ser Ala Leu Lys Lys Ile Phe Val Asp Gly Asp Ser Leu Phe Glu
                530                 535                 540
Tyr Leu His Ala Gln Thr Phe Pro Ser Asn Ile Glu Asn Leu Gln Leu
545                 550                 555                 560
Thr Asn Ser Leu Asn Asp Ala Leu Arg Asn Asn Asn Lys Val Tyr Thr
                565                 570                 575
Phe Phe Ser Thr Asn Leu Val Glu Lys Ala Asn Thr Val Val Gly Ala
                580                 585                 590
Ser Leu Phe Val Asn Trp Val Lys Gly Val Ile Asp Asp Phe Thr Ser
                595                 600                 605
Glu Ser Thr Gln Lys Ser Thr Ile Asp Lys Val Ser Asp Val Ser Ile
                610                 615                 620
Ile Ile Pro Tyr Ile Gly Pro Ala Leu Asn Val Gly Asn Glu Thr Ala
625                 630                 635                 640
Lys Glu Asn Phe Lys Asn Ala Phe Glu Ile Gly Gly Ala Ala Ile Leu
                645                 650                 655
Met Glu Phe Ile Pro Glu Leu Ile Val Pro Ile Val Gly Phe Phe Thr
                660                 665                 670
Leu Glu Ser Tyr Val Gly Asn Lys Gly His Ile Ile Met Thr Ile Ser
                675                 680                 685
Asn Ala Leu Lys Lys Arg Asp Gln Lys Trp Thr Asp Met Tyr Gly Leu
                690                 695                 700
Ile Val Ser Gln Trp Leu Ser Thr Val Asn Thr Gln Phe Tyr Thr Ile
705                 710                 715                 720
Lys Glu Arg Met Tyr Asn Ala Leu Asn Asn Gln Ser Gln Ala Ile Glu
                725                 730                 735
Lys Ile Ile Glu Asp Gln Tyr Asn Arg Tyr Ser Glu Glu Asp Lys Met
                740                 745                 750
Asn Ile Asn Ile Asp Phe Asn Asp Ile Asp Phe Lys Leu Asn Gln Ser
                755                 760                 765
Ile Asn Leu Ala Ile Asn Asn Ile Asp Asp Phe Ile Asn Gln Cys Ser
                770                 775                 780
```

```
Ile Ser Tyr Leu Met Asn Arg Met Ile Pro Leu Ala Val Lys Lys Leu
785                 790                 795                 800

Lys Asp Phe Asp Asp Asn Leu Lys Arg Asp Leu Leu Glu Tyr Ile Asp
            805                 810                 815

Thr Asn Glu Leu Tyr Leu Leu Asp Glu Val Asn Ile Leu Lys Ser Lys
        820                 825                 830

Val Asn Arg His Leu Lys Asp Ser Ile Pro Phe Asp Leu Ser Leu Tyr
    835                 840                 845

Thr Lys Asp Thr Ile Leu Ile Gln Val Phe Asn Asn Tyr Ile Ser Asn
850                 855                 860

Ile Ser Ser Asn Ala Ile Leu Ser Leu Ser Tyr Arg Gly Gly Arg Leu
865                 870                 875                 880

Ile Asp Ser Ser Gly Tyr Gly Ala Thr Met Asn Val Gly Ser Asp Val
            885                 890                 895

Ile Phe Asn Asp Ile Gly Asn Gly Gln Phe Lys Leu Asn Asn Ser Glu
        900                 905                 910

Asn Ser Asn Ile Thr Ala His Gln Ser Lys Phe Val Val Tyr Asp Ser
    915                 920                 925

Met Phe Asp Asn Phe Ser Ile Asn Phe Trp Val Arg Thr Pro Lys Tyr
930                 935                 940

Asn Asn Asn Asp Ile Gln Thr Tyr Leu Gln Asn Glu Tyr Thr Ile Ile
945                 950                 955                 960

Ser Cys Ile Lys Asn Asp Ser Gly Trp Lys Val Ser Ile Lys Gly Asn
            965                 970                 975

Arg Ile Ile Trp Thr Leu Ile Asp Val Asn Ala Lys Ser Lys Ser Ile
        980                 985                 990

Phe Phe Glu Tyr Ser Ile Lys Asp Asn Ile Ser Asp Tyr Ile Asn Lys
    995                 1000                1005

Trp Phe Ser Ile Thr Ile Thr Asn Asp Arg Leu Gly Asn Ala Asn
    1010                1015                1020

Ile Tyr Ile Asn Gly Ser Leu Lys Lys Ser Glu Lys Ile Leu Asn
    1025                1030                1035

Leu Asp Arg Ile Asn Ser Ser Asn Asp Ile Asp Phe Lys Leu Ile
    1040                1045                1050

Asn Cys Thr Asp Thr Thr Lys Phe Val Trp Ile Lys Asp Phe Asn
    1055                1060                1065

Ile Phe Gly Arg Glu Leu Asn Ala Thr Glu Val Ser Ser Leu Tyr
    1070                1075                1080

Trp Ile Gln Ser Ser Thr Asn Thr Leu Lys Asp Phe Trp Gly Asn
    1085                1090                1095

Pro Leu Arg Tyr Asp Thr Gln Tyr Tyr Leu Phe Asn Gln Gly Met
    1100                1105                1110

Gln Asn Ile Tyr Ile Lys Tyr Phe Ser Lys Ala Ser Met Gly Glu
    1115                1120                1125

Thr Ala Pro Arg Thr Asn Phe Asn Asn Ala Ala Ile Asn Tyr Gln
    1130                1135                1140

Asn Leu Tyr Leu Gly Leu Arg Phe Ile Ile Lys Lys Ala Ser Asn
    1145                1150                1155

Ser Arg Asn Ile Asn Asn Asp Asn Ile Val Arg Glu Gly Asp Tyr
    1160                1165                1170

Ile Tyr Leu Asn Ile Asp Asn Ile Ser Asp Glu Ser Tyr Arg Val
    1175                1180                1185

Tyr Val Leu Val Asn Ser Lys Glu Ile Gln Thr Gln Leu Phe Leu
    1190                1195                1200
```

```
Ala Pro Ile Asn Asp Asp Pro Thr Phe Tyr Asp Val Leu Gln Ile
    1205                1210                1215

Lys Lys Tyr Tyr Glu Lys Thr Thr Tyr Asn Cys Gln Ile Leu Cys
1220                1225                1230

Glu Lys Asp Thr Lys Thr Phe Gly Leu Phe Gly Ile Gly Lys Phe
    1235                1240                1245

Val Lys Asp Tyr Gly Tyr Val Trp Asp Thr Tyr Asp Asn Tyr Phe
    1250                1255                1260

Cys Ile Ser Gln Trp Tyr Leu Arg Arg Ile Ser Glu Asn Ile Asn
    1265                1270                1275

Lys Leu Arg Leu Gly Cys Asn Trp Gln Phe Ile Pro Val Asp Glu
    1280                1285                1290

Gly Trp Thr Glu
    1295

<210> SEQ ID NO 24
<211> LENGTH: 1315
<212> TYPE: PRT
<213> ORGANISM: Clostridium tetani

<400> SEQUENCE: 24

Met Pro Ile Thr Ile Asn Asn Phe Arg Tyr Ser Asp Pro Val Asn Asn
1               5                   10                  15

Asp Thr Ile Ile Met Met Glu Pro Pro Tyr Cys Lys Gly Leu Asp Ile
            20                  25                  30

Tyr Tyr Lys Ala Phe Lys Ile Thr Asp Arg Ile Trp Ile Val Pro Glu
        35                  40                  45

Arg Tyr Glu Phe Gly Thr Lys Pro Glu Asp Phe Asn Pro Pro Ser Ser
    50                  55                  60

Leu Ile Glu Gly Ala Ser Glu Tyr Tyr Asp Pro Asn Tyr Leu Arg Thr
65                  70                  75                  80

Asp Ser Asp Lys Asp Arg Phe Leu Gln Thr Met Val Lys Leu Phe Asn
                85                  90                  95

Arg Ile Lys Asn Asn Val Ala Gly Glu Ala Leu Leu Asp Lys Ile Ile
            100                 105                 110

Asn Ala Ile Pro Tyr Leu Gly Asn Ser Tyr Ser Leu Leu Asp Lys Phe
        115                 120                 125

Asp Thr Asn Ser Asn Ser Val Ser Phe Asn Leu Leu Glu Gln Asp Pro
    130                 135                 140

Ser Gly Ala Thr Thr Lys Ser Ala Met Leu Thr Asn Leu Ile Ile Phe
145                 150                 155                 160

Gly Pro Gly Pro Val Leu Asn Lys Asn Glu Val Arg Gly Ile Val Leu
                165                 170                 175

Arg Val Asp Asn Lys Asn Tyr Phe Pro Cys Arg Asp Gly Phe Gly Ser
            180                 185                 190

Ile Met Gln Met Ala Phe Cys Pro Glu Tyr Val Pro Thr Phe Asp Asn
        195                 200                 205

Val Ile Glu Asn Ile Thr Ser Leu Thr Ile Gly Lys Ser Lys Tyr Phe
    210                 215                 220

Gln Asp Pro Ala Leu Leu Leu Met His Glu Leu Ile His Val Leu His
225                 230                 235                 240

Gly Leu Tyr Gly Met Gln Val Ser Ser His Glu Ile Ile Pro Ser Lys
                245                 250                 255
```

```
Gln Glu Ile Tyr Met Gln His Thr Tyr Pro Ile Ser Ala Glu Glu Leu
            260                 265                 270

Phe Thr Phe Gly Gly Gln Asp Ala Asn Leu Ile Ser Ile Asp Ile Lys
            275                 280                 285

Asn Asp Leu Tyr Glu Lys Thr Leu Asn Asp Tyr Lys Ala Ile Ala Asn
            290                 295                 300

Lys Leu Ser Gln Val Thr Ser Cys Asn Asp Pro Asn Ile Asp Ile Asp
305                 310                 315                 320

Ser Tyr Lys Gln Ile Tyr Gln Gln Lys Tyr Gln Phe Asp Lys Asp Ser
            325                 330                 335

Asn Gly Gln Tyr Ile Val Asn Glu Asp Lys Phe Gln Ile Leu Tyr Asn
            340                 345                 350

Ser Ile Met Tyr Gly Phe Thr Glu Ile Glu Leu Gly Lys Lys Phe Asn
            355                 360                 365

Ile Lys Thr Arg Leu Ser Tyr Phe Ser Met Asn His Asp Pro Val Lys
            370                 375                 380

Ile Pro Asn Leu Leu Asp Asp Thr Ile Tyr Asn Asp Thr Glu Gly Phe
385                 390                 395                 400

Asn Ile Glu Ser Lys Asp Leu Lys Ser Glu Tyr Lys Gly Gln Asn Met
            405                 410                 415

Arg Val Asn Thr Asn Ala Phe Arg Asn Val Asp Gly Ser Gly Leu Val
            420                 425                 430

Ser Lys Leu Ile Gly Leu Cys Lys Lys Ile Ile Pro Pro Thr Asn Ile
            435                 440                 445

Arg Glu Asn Leu Tyr Asn Arg Thr Ala Ser Leu Thr Asp Leu Gly Gly
            450                 455                 460

Glu Leu Cys Ile Lys Ile Lys Asn Glu Asp Leu Thr Phe Ile Ala Glu
465                 470                 475                 480

Lys Asn Ser Phe Ser Glu Glu Pro Phe Gln Asp Glu Ile Val Ser Tyr
            485                 490                 495

Asn Thr Lys Asn Lys Pro Leu Asn Phe Asn Tyr Ser Leu Asp Lys Ile
            500                 505                 510

Ile Val Asp Tyr Asn Leu Gln Ser Lys Ile Thr Leu Pro Asn Asp Arg
            515                 520                 525

Thr Thr Pro Val Thr Lys Gly Ile Pro Tyr Ala Pro Glu Tyr Lys Ser
            530                 535                 540

Asn Ala Ala Ser Thr Ile Glu Ile His Asn Ile Asp Asp Asn Thr Ile
545                 550                 555                 560

Tyr Gln Tyr Leu Tyr Ala Gln Lys Ser Pro Thr Thr Leu Gln Arg Ile
            565                 570                 575

Thr Met Thr Asn Ser Val Asp Asp Ala Leu Ile Asn Ser Thr Lys Ile
            580                 585                 590

Tyr Ser Tyr Phe Pro Ser Val Ile Ser Lys Val Asn Gln Gly Ala Gln
            595                 600                 605

Gly Ile Leu Phe Leu Gln Trp Val Arg Asp Ile Ile Asp Asp Phe Thr
            610                 615                 620

Asn Glu Ser Ser Gln Lys Thr Thr Ile Asp Lys Ile Ser Asp Val Ser
625                 630                 635                 640

Thr Ile Val Pro Tyr Ile Gly Pro Ala Leu Asn Ile Val Lys Gln Gly
            645                 650                 655
```

```
Tyr Glu Gly Asn Phe Ile Gly Ala Leu Glu Thr Thr Gly Val Val Leu
            660                 665                 670

Leu Leu Glu Tyr Ile Pro Glu Ile Thr Leu Pro Val Ile Ala Ala Leu
            675                 680                 685

Ser Ile Ala Glu Ser Ser Thr Gln Lys Glu Lys Ile Ile Lys Thr Ile
690                 695                 700

Asp Asn Phe Leu Glu Lys Arg Tyr Glu Lys Trp Ile Glu Val Tyr Lys
705                 710                 715                 720

Leu Val Lys Ala Lys Trp Leu Gly Thr Val Asn Thr Gln Phe Gln Lys
                725                 730                 735

Arg Ser Tyr Gln Met Tyr Arg Ser Leu Glu Tyr Gln Val Asp Ala Ile
                740                 745                 750

Lys Lys Ile Ile Asp Tyr Glu Tyr Lys Ile Tyr Ser Gly Pro Asp Lys
                755                 760                 765

Glu Gln Ile Ala Asp Glu Ile Asn Asn Leu Lys Asn Lys Leu Glu Glu
            770                 775                 780

Lys Ala Asn Lys Ala Met Ile Asn Ile Asn Ile Phe Met Arg Glu Ser
785                 790                 795                 800

Ser Arg Ser Phe Leu Val Asn Gln Met Ile Asn Glu Ala Lys Lys Gln
                805                 810                 815

Leu Leu Glu Phe Asp Thr Gln Ser Lys Asn Ile Leu Met Gln Tyr Ile
                820                 825                 830

Lys Ala Asn Ser Lys Phe Ile Gly Ile Thr Glu Leu Lys Lys Leu Glu
            835                 840                 845

Ser Lys Ile Asn Lys Val Phe Ser Thr Pro Ile Pro Phe Ser Tyr Ser
850                 855                 860

Lys Asn Leu Asp Cys Trp Val Asp Asn Glu Glu Asp Ile Asp Val Ile
865                 870                 875                 880

Leu Lys Lys Ser Thr Ile Leu Asn Leu Asp Ile Asn Asn Asp Ile Ile
                885                 890                 895

Ser Asp Ile Ser Gly Phe Asn Ser Ser Val Ile Thr Tyr Pro Asp Ala
            900                 905                 910

Gln Leu Val Pro Gly Ile Asn Gly Lys Ala Ile His Leu Val Asn Asn
            915                 920                 925

Glu Ser Ser Glu Val Ile Val His Lys Ala Met Asp Ile Glu Tyr Asn
930                 935                 940

Asp Met Phe Asn Asn Phe Thr Val Ser Phe Trp Leu Arg Val Pro Lys
945                 950                 955                 960

Val Ser Ala Ser His Leu Glu Gln Tyr Gly Thr Asn Glu Tyr Ser Ile
                965                 970                 975

Ile Ser Ser Met Lys Lys His Ser Leu Ser Ile Gly Ser Gly Trp Ser
                980                 985                 990

Val Ser Leu Lys Gly Asn Asn Leu Ile Trp Thr Leu Lys Asp Ser Ala
                995                 1000                1005

Gly Glu Val Arg Gln Ile Thr Phe Arg Asp Leu Pro Asp Lys Phe
    1010                1015                1020

Asn Ala Tyr Leu Ala Asn Lys Trp Val Phe Ile Thr Ile Thr Asn
    1025                1030                1035

Asp Arg Leu Ser Ser Ala Asn Leu Tyr Ile Asn Gly Val Leu Met
    1040                1045                1050

Gly Ser Ala Glu Ile Thr Gly Leu Gly Ala Ile Arg Glu Asp Asn
    1055                1060                1065
```

```
Asn Ile Thr Leu Lys Leu Asp Arg Cys Asn Asn Asn Gln Tyr
    1070            1075                1080

Val Ser Ile Asp Lys Phe Arg Ile Phe Cys Lys Ala Leu Asn Pro
    1085            1090                1095

Lys Glu Ile Glu Lys Leu Tyr Thr Ser Tyr Leu Ser Ile Thr Phe
    1100            1105                1110

Leu Arg Asp Phe Trp Gly Asn Pro Leu Arg Tyr Asp Thr Glu Tyr
    1115            1120                1125

Tyr Leu Ile Pro Val Ala Ser Ser Lys Asp Val Gln Leu Lys
    1130            1135                1140

Asn Ile Thr Asp Tyr Met Tyr Leu Thr Asn Ala Pro Ser Tyr Thr
    1145            1150                1155

Asn Gly Lys Leu Asn Ile Tyr Tyr Arg Arg Leu Tyr Asn Gly Leu
    1160            1165                1170

Lys Phe Ile Ile Lys Arg Tyr Thr Pro Asn Asn Glu Ile Asp Ser
    1175            1180                1185

Phe Val Lys Ser Gly Asp Phe Ile Lys Leu Tyr Val Ser Tyr Asn
    1190            1195                1200

Asn Asn Glu His Ile Val Gly Tyr Pro Lys Asp Gly Asn Ala Phe
    1205            1210                1215

Asn Asn Leu Asp Arg Ile Leu Arg Val Gly Tyr Asn Ala Pro Gly
    1220            1225                1230

Ile Pro Leu Tyr Lys Lys Met Glu Ala Val Lys Leu Arg Asp Leu
    1235            1240                1245

Lys Thr Tyr Ser Val Gln Leu Lys Leu Tyr Asp Asp Lys Asn Ala
    1250            1255                1260

Ser Leu Gly Leu Val Gly Thr His Asn Gly Gln Ile Gly Asn Asp
    1265            1270                1275

Pro Asn Arg Asp Ile Leu Ile Ala Ser Asn Trp Tyr Phe Asn His
    1280            1285                1290

Leu Lys Asp Lys Ile Leu Gly Cys Asp Trp Tyr Phe Val Pro Thr
    1295            1300                1305

Asp Glu Gly Trp Thr Asn Asp
    1310            1315

<210> SEQ ID NO 25
<211> LENGTH: 17
<212> TYPE: PRT
<213> ORGANISM: artificial sequence
<220> FEATURE:
<223> OTHER INFORMATION: completely synthesized peptide

<400> SEQUENCE: 25

Ser Asn Lys Thr Arg Ile Asp Glu Ala Asn Gln Arg Ala Thr Lys Met
1               5                   10                  15

Leu

<210> SEQ ID NO 26
<211> LENGTH: 6
<212> TYPE: PRT
<213> ORGANISM: artificial sequence
<220> FEATURE:
<223> OTHER INFORMATION: completely synthesized peptide

<400> SEQUENCE: 26

Arg Ala Thr Lys Met Leu
1               5
```

MEANS AND METHODS FOR THE DETERMINATION OF THE AMOUNT OF NEUROTOXIN POLYPEPTIDE AND OF ITS CATALYTIC AND PROTEOLYTIC ACTIVITIES

The present invention pertains to the field of tools for ensuring manufacture of polypeptides and quality control. Specifically, it relates to a method for determining of the amount of processed (active) Neurotoxin polypeptide in a solution comprising processed Neurotoxin polypeptide and partially processed or unprocessed Neurotoxin polypeptide. The present invention relates further to a device for determining said amount and a kit adapted to carry out the method of the present invention.

*Clostridium botulinum* and *Clostridium tetani* produce highly potent neurotoxins, i.e. *botulinum* toxins (BoNTs) and tetanus toxin (TeNT), respectively. These Clostridial Neurotoxins (CNTs) specifically bind to neuronal cells and disrupt neurotransmitter release. Each toxin is synthesized as an inactive unprocessed approximately 150 kDa single-chain protein. The posttranslational processing involves formation of disulfide bridges, and limited proteolysis (nicking) by the bacterial protease(s). Active Neurotoxin consists of two chains, an N-terminal light chain of approx. 50 kDa and a heavy chain of approx. 100 kDa linked by a disulfide bond. CNTs structurally and functionally consist of three domains, i.e. the catalytic light chain, the heavy chain encompassing the translocation domain (N-terminal half) and the receptor binding domain (C-terminal half), see Krieglstein 1990, Eur J Biochem 188, 39; Krieglstein 1991, Eur J Biochem 202, 41; Krieglstein 1994, J Protein Chem 13, 49. The *Botulinum* Neurotoxins are synthesized as molecular complexes comprising the 150 kDa Neurotoxin protein and associated non-toxic proteins. The complex sizes differ based on the Clostridial strain and the distinct Neurotoxin serotypes ranging from 300 kDa, over 500 kDa, and 900 kDa. The non-toxic proteins in these complexes stabilize the Neurotoxin and protect it against degradation, see Silberstein 2004, Pain Practice 4, S19-S26.

*Clostridium botulinum* secretes seven antigenically distinct serotypes designated A to G of the *botulinum* neurotoxin (BoNT). All serotypes together with the related tetanus neurotoxin (TeNT) secreted by *Clostridium tetani*, are Zn2+-endoproteases that block synaptic exocytosis by cleaving SNARE proteins, see Couesnon, 2006, Microbiology, 152, 759. CNTs cause the flaccid muscular paralysis seen in botulism and tetanus, see Fischer 2007, PNAS 104, 10447.

Despite its toxic effects, *botulinum* toxin complex has been used as a therapeutic agent in a large number of diseases. *Botulinum* toxin serotype A was approved for human use in the United States in 1989 for the treatment of strabism, blepharospasm, and other disorders. It is commercially available as *Botulinum* toxin A protein preparation, for example, under the tradename BOTOX (Allergan Inc) or under the tradename DYSPORT (Ipsen Ltd). An improved, complex-free *Botulinum* toxin A preparation is commercially available under the tradename XEOMIN (Merz Pharmaceuticals GmbH). For therapeutic applications, the preparation is injected directly into the muscle to be treated. At physiological pH, the toxin is released from the protein complex and the desired pharmacological effect takes place. The effect of *Botulinum* toxin is only temporary, which is the reason why repeated administration of *Botulinum* toxin may be required to maintain a therapeutic affect.

The Clostridial Neurotoxins weaken voluntary muscle strength and are effective therapy for strabism, focal dystonia, including cervical dystonia, and benign essential blepharospasm. They have been further shown to relief hemifacial spasm, and focal spasticity, and moreover, to be effective in a wide range of other indications, such as gastrointestinal disorders, hyperhidrosis, and cosmetic wrinkle correction, see Jost 2007, Drugs 67, 669.

During the manufacturing process of Clostridial Neurotoxins, the qualitative and quantitative determination as well as the quality control of the active Neurotoxin polypeptide is of particular importance. Currently available Neurotoxin preparations comprise, in addition to the desired active (processed or mature) Neurotoxin, a proteolytically unprocessed precursor and/or partially processed Neurotoxin polypeptide. The proteolytically unprocessed precursor or partially processed Neurotoxin polypeptide differs from the mature (active, processed) Neurotoxin polypeptide in a sequence of only a few amino acids. Therefore, they can hardly be quantitatively distinguished based on their chemical and physical properties. On the other hand, the portion of proteolytically unprocessed precursor and/or partially processed Neurotoxin polypeptide of the total protein may still be significant in such preparations. The portion depends on the biological system used for the production and results from the biosynthesis and the conditions of the fermentation process. Thus, the amount of desired mature, biologically active Neurotoxin polypeptide in Neurotoxin preparations is predefined and, currently, rather difficult to determine.

Means and methods for a reliable qualitative and quantitative detection system of mature (active) Neurotoxin polypeptide are highly desirable but not yet available.

Thus, the technical problem underlying the present invention may be seen as the provision of means and methods complying with the aforementioned needs. The technical problem is solved by the embodiments characterized in the claims and herein below.

The present invention relates to a method for determining the amount of processed (active) Neurotoxin polypeptide in a solution comprising processed Neurotoxin polypeptide and partially processed and/or unprocessed Neurotoxin polypeptide comprising the steps of:

a) contacting a first portion of said solution with a first capture antibody which specifically binds to the light chains of mature Neurotoxin polypeptide, partially processed, and unprocessed Neurotoxin polypeptide under conditions which allow for binding of said antibody to said mature Neurotoxin, partially processed, and unprocessed Neurotoxin polypeptide, thus forming a first antibody-complex, b) contacting the first antibody complex with a detection antibody which specifically binds to the heavy chain of said mature Neurotoxin, partially processed, and unprocessed Neurotoxin polypeptide in the antibody complex formed in step a), whereby a first detection complex is formed, c) contacting a second portion of said solution with a second capture antibody which specifically binds to the linkers of said partially processed and unprocessed Neurotoxin polypeptide under conditions which allow for binding of said antibody to said partially processed and unprocessed Neurotoxin polypeptide, and thus forming a second antibody-complex, d) contacting the second antibody-complex with the detection antibody, whereby a second detection complex is formed, e) determining the amount of the second detection complex formed in steps b) and d), and f) calculating the amount of mature Neurotoxin polypeptide based on the amounts of the first and second detection complex determined in step e).

The aforementioned method may, in general, comprise additional steps including steps for the preparation of the solution or steps concerning the further evaluation of the results obtained in step f). Moreover, the steps a) and b) as well as steps c) and d) may be carried out simultaneously or sequentially. In the latter case, steps a) and b) can be carried out prior or after steps c) and d). Further the determination referred to in step e) may be carried out in said case after both series of steps have been carried out or the determination in step e) as far as the first detection complex will be concerned is carried out after steps a) and b) while the determination concerning the second detection complex is carried out after steps c) and d). The method may in part or entirely be assisted by automation. The incubation and measurement steps can be carried out by, e.g., a robot. The data analysis and interpretation can be carried out by a computer-implemented calculation algorithm.

The term "Neurotoxin polypeptide" as used in the present invention refers to the seven distinct serotypes of *Botulinum* Neurotoxins, i.e. BoNT/A, BoNT/B, BoNT/C1, BoNT/D, BoNT/E, BoNT/F, BoNT/G, and to Tetanus Neurotoxin (TeNT), see Table 1, and variants thereof.

TABLE 1

Botulinum and Tetanus Neurotoxins

| SEQ ID NO: | Reference | Accession-NO: | Neurotoxin (full length)/ Bacterial Strain |
|---|---|---|---|
| 17 | Beecher 1997, J Protein Chem 16, 701-712.; Krieglstein 1994, J Protein Chem 13, 49-57. | ABD65472.1 GI: 89258592 | BoNT/A (Hall/62A) |
| 18 | Antharavally 1998, J Protein Chem 17, 417-428. | BAE48264.1 GI: 81230332 | BoNT/B (Okra) |
| 19 | Sagane 1999, J Protein Chem 18, 885-892. | BAA89713.1 GI: 6729213 | BoNT/C1 (C-6814) |
| 20 | Sagane 1999, J Protein Chem 18, 885-892. | BAA90661.1 GI: 6939795 | BoNT/D (CB16) |
| 21 | Antharavally 1997, J Protein Chem 16, 787-799. | CAA43999.1 GI: 40394 | BoNT/E (Beluga) |
| 22 | Sagane 1999, J Protein Chem 18, 885-892. | CAA73972.1 GI: 3805790 | BoNT/F (NCTC10281) |
| 23 | Campbell 1993, Biochim. Biophys. Acta 1216 (3), 487-491 | CAA52275.1 GI: 441276 | BoNT/G |
| 24 | Krieglstein 1991, *Eur J Biochem* 202, 41-51.; Krieglstein et al. 1990, Eur J Biochem 188, 39-45. | P04958.2 GI: 135624 | TeNT |

The Neurotoxins referred to herein, in principle, comprise an N-terminal light chain and a C-terminal heavy chain. The Neurotoxins are produced as single chain precursor molecules, herein referred to as "unprocessed Neurotoxin polypeptides". The N-terminal light chain and the C-terminal heavy chain sequences are separated in the unprocessed Neurotoxins by at least one proteolytic cleavage site. These Neurotoxins contain a linker sequence between the light and heavy chain sequences, wherein the light chain is located N-terminally starting from the first cleavage site and the heavy chain is located C-terminally starting from the second cleavage site. In an aspect of the invention, said linker has an amino acid sequence as shown in any one of SEQ ID NOs: 1 to 16. During processing of the Neurotoxins, the linker sequence will be excised. These Neurotoxins contain two proteolytic cleavage sites, one at the N-terminal and one at the C-terminal end of the linker sequences. During processing of such Neurotoxins, intermediates may occur which are cleaved on either cleavage site, i.e. the linker sequence will not be yet excised but remains on either the N-terminal light chain or the C-terminal heavy chain. Such intermediates are referred to as "partially processed Neurotoxin polypeptides" in this specification. Other Neurotoxins, merely, contain one cleavage site. For those Neutrotoxins it will be understood that no linker sequence can be excised. Nevertheless, the unprocessed Neurotoxin can be immunologically recognized by an intact proteolytic cleavage site and flanking sequences. These flanking sequences and the cleavage site are also deemed to be a linker for the purpose of the present invention. Thus, the term "linker" as used herein and specified above refers either to the sequence between the light and heavy chain sequences for Neurotoxin polypeptides having two cleavage sites or to the cleavage site and flanking sequences for Neurotoxin polypeptides having only a single cleavage site. As a result of the processing, "processed Neurotoxin polypeptide" is obtained. The said processed Neurotoxin polypeptide exhibits the biological properties characteristic for a Neurotoxin, namely, (a) receptor binding, (b) internalization, (c) translocation across the endosomal membrane into the cytosol, and/or (d) endoproteolytic cleavage of proteins involved in synaptic vesicle membrane fusion. Therefore, the processed Neurotoxin polypeptide is sometimes referred to herein as active or mature Neurotoxin polypeptide. The biological activity of the Neurotoxin polypeptides, in an aspect, results from all of the aforementioned biological properties. In vivo assays for assessing biological activity include the mouse LD50 assay and the ex vivo mouse hemidiaphragm assay as described by Pearce et al. and Dressier et al. (Pearce 1994, Toxicol Appl Pharmacol 128: 69-77 and Dressier 2005, Mov Disord 20:1617-1619). The biological activity is commonly expressed in Mouse Units (MU). As used herein, 1 MU is the amount of neurotoxic component, which kills 50% of a specified mouse population after intraperitoneal injection, i.e. the mouse i.p. LD50.

In an aspect of the method of the invention, the said Neurotoxin polypeptide is selected from the group consisting of: a) a Neurotoxin polypeptide having an amino acid sequence as shown in any one of SEQ ID NOs: 17 to 24, and b) a Neurotoxin polypeptide having an amino acid sequence being at least 40% identical to the amino acid sequence of the Neurotoxin polypeptide as shown in any one of SEQ ID NOs: 17 to 24. The aforementioned amino acid sequences show unprocessed Neurotoxin polypeptides. The sequences of the corresponding partially processed or processed Neurotoxin polypeptides can be deduced from the said sequences by the information on cleavage sites provided in Table 3, below. In another aspect of the invention, the Neurotoxin polypeptide has an amino acid sequence being at least 40%, at least 50%, at least 60%, at least 70%, at least 75%, at least 80%, at least 85%, at least 90%, at least 95%, at least 98% or at least 99% sequence identical to the amino acid sequence as shown in SEQ ID NOs: 17 to 24. Identical as used in the present invention refers to sequence identity of amino acid sequences wherein the sequences are aligned so that the highest order match is obtained. This can be achieved by using published techniques or methods codified in computer programs such as, for example, BLASTP, BLASTN, FASTA, Altschul 1990, J Mol Biol 215, 403. The percent identity values are, in one aspect, calculated over the entire amino acid sequence. A series of programs based on a variety of algorithms is available to the skilled worker for comparing different sequences.

In this context, the algorithms of Needleman and Wunsch or Smith and Waterman give particularly reliable results. To carry out the sequence alignments, the program PileUp (1987, J Mol Evolution 25, 351; Higgins 1989 CABIOS 5, 151) or the programs Gap and BestFit (Needleman and Wunsch 1970, J Mol Biol 48; 443; Smith and Waterman 1981, Adv Appl Math 2, 482), which are part of the GCG software packet (Genetics Computer Group 1991, 575 Science Drive, Madison, Wis., USA 53711), are to be used. The sequence identity values recited above in percent (%) are to be determined, in one aspect of the invention, using the program GAP over the entire sequence region with the following settings: Gap Weight: 50, Length Weight: 3, Average Match: 10.000 and Average Mismatch: 0.000, which, unless otherwise specified, shall always be used as standard settings for sequence alignments. It will be understood that the aforementioned variants shall, in an aspect of the invention, retain, at least one of the biological properties of Neurotoxins and, in an aspect, all of the biological properties of a Neurotoxin polypeptide recited herein. In a further aspect, the variants can be Neurotoxins having improved or altered biological properties, e.g., they may comprise cleavage sites which are improved for enzyme recognition or may be improved for receptor binding or any other property specified above. It is conceivable that the concept of the present invention relies on the presence of two or more cleavage sites between light and heavy chain of the Neurotoxin polypeptide while the nature of the cleavage sites and the particular amino acid sequence between them does not matter as long as the agent is specific for the partially processed or unprocessed Neurotoxin polypeptide. Accordingly, it is another aspect, to replace protease recognition sites and the linker peptide between heavy- and light chain of the Neurotoxin polypeptide.

In another aspect, the Neurotoxin polypeptide in accordance with the method of the invention may be a chimeric molecule. Such said chimeric molecule, in one aspect, may have single domains substituted. Accordingly, in another aspect, the portion of the Neurotoxin heavy chain is replaced by a portion of an FC domain of an antibody.

The term "amount" as used in the method of the present invention encompasses the absolute amount of a polypeptide, the relative amount or the concentration of the said polypeptide as well as any value or parameter which correlates thereto or can be derived therefrom.

The term "solution" as used herein refers to any solvent system containing mature Neurotoxin polypeptide and its partially processed and/or unprocessed Neurotoxin polypeptide precursors. The solvent system furthermore comprises a solvent. The solvents encompassed, in various aspects of the invention, are water, aqueous buffer systems, organic solvents, and ionic liquids. In one aspect of the invention, it is an aqueous solvent system. Moreover, the solvent system, in addition to the mature Neurotoxin polypeptide and the partially processed or unprocessed precursor Neurotoxin polypeptide and the solvent may comprise further molecules as well, including further bacterial polypeptides. In an aspect, the solution to be applied in the method of the present invention will be a bacterial cell culture or a partially purified or purified preparation obtained from such a bacterial cell culture.

The term "portion" as used in accordance with the method of the invention, refers to a sample or aliquot of the solution. In an aspect of the method of the invention, the first portion and the second portion referred to in this invention are essentially equal in their volume and contents. This can be achieved, e.g., by measuring the total protein content of the first and second portion, whereby an essentially identical total protein content is indicative for a first and second portion having essentially the same contents. However, in a further aspect, a portion to be applied as a first or second portion may be a dilution of the sample or aliquot of the solution. It will be understood that dependent on the amount of the Neurotoxin polypeptide to be determined (i.e. partially processed or unprocessed Neurotoxin polypeptide or total Neurotoxin), a dilution might become necessary in order to allow for an optimal qualitative and quantitative determination. How to make such dilutions is well known to those skilled in the art.

The term "contacting" as used in accordance with the method of the invention refers to (i) bringing the aforementioned capture antibodies and the Neurotoxins comprised by the solution or (ii) bringing the antibody-complexes and the detection antibodies in physical proximity as to allow physical and/or chemical interaction. Suitable conditions which allow for specific interaction are well known to the skilled worker. Said conditions will depend on the antibodies and the solution to be applied in the method of the present invention and can be adapted by the skilled artisan without further ado. Moreover, a time being sufficient to allow interaction can also be determined by the skilled worker without further ado. Moreover, it is to be understood that between the individual steps of contacting recited in the method of the present invention, washing steps may be performed in order to obtain suitable conditions for contacting. For example, after formation of a first antibody-complex in step a), the remaining solution shall be removed prior to applying the detection antibody to the said antibody-complex. Furthermore, after the first detection-complex is formed in step b), it might be necessary to remove the remaining (uncomplexed) detection antibody prior to determining the amount of the first detection-complex in step c). The same applies, of course, for steps d) to f), accordingly.

An "antibody" as used herein encompasses a monoclonal antibody, a polyclonal antibody, a single chain antibody, a chimerized antibody, a bispecific antibody, a synthetic antibody, or a fragment of any of said antibodies. Fragments of said antibodies include Fab, Fv, or scFv fragments, or chemically modified derivatives of any of these fragments. Antibodies can be manufactured by using methods which are described, e.g., in Harlow and Lane "Antibodies, A Laboratory Manual", CSH Press, Cold Spring Harbor, 1988. Monoclonal antibodies can be prepared by the techniques originally described in Köhler 1975, Nature 256, 495, and Galfré 1981, Meth Enzymol 73, 3. Said techniques comprise the fusion of mouse myeloma cells to spleen cells derived from immunized mammals. Antibodies can be further improved by techniques well known in the art. For example, surface plasmon resonance as employed in the BIACORE® system can be used to increase the efficiency of phage antibodies which bind to the epitope, see Schier 1996, Human Antibodies Hybridomas 7, 97; Malmborg 1995, J. Immunol Methods 183, 7. Antibodies as used herein also comprise functional equivalents of antibodies, i.e. agents which are capable of specifically binding to the desired epitopes or parts of the Neurotoxin polypeptides. In an aspect, such functional equivalents comprise the receptor or binding proteins referred to elsewhere in this specification or domains thereof which are capable of mediating the said specific binding.

According to the method of the present invention, the "first capture antibody" specifically binds to epitopes comprised by the light chain of mature Neurotoxin polypeptide and comprised by the partially processed and/or unprocessed Neurotoxin polypeptide. Specific binding as used herein, in general, means that the antibody does not cross react to a significant extent with other epitopes on the heavy chain or the linker of the Neurotoxin polypeptide to be determined or on other polypeptides. Specific binding as referred to herein can be tested by various well known techniques including, e.g., competition experiments and Western blots. An epitope as used in accordance with the invention relates to the antigenic determinant which is recognized by the antibody.

In another aspect the, different capture antibodies can be used to replace the first capture antibody. To this end, at least one capture antibody specifically binds to epitopes of the light chain of the unprocessed Neurotoxin polypeptide, at least one further capture antibody specifically binds to epitopes of the light chain of the partially processed Neurotoxin polypeptide and at least one further capture antibody specifically binds to epitopes of the light chain of the processed Neurotoxin polypeptide may be applied. It will be understood that these three types of antibodies functionally resemble the first capture antibody for the purpose of the method of the present invention. Similarly, a capture antibody which specifically binds to epitopes of the light chain of partially processed and unprocessed Neurotoxin polypeptide can be used in combination with a capture antibody specifically binds to epitopes of the light chain of the processed Neurotoxin polypeptide.

The said first capture antibody shall, in an aspect, be immobilized. Said immobilization of an antibody, in principle, can be achieved, in an aspect, by reversible or non-reversible, direct or indirect (via linker molecules) binding of the antibody to a solid support. In an aspect the first capture antibody is immobilized prior to carrying out the method. In another aspect, the first capture antibody is immobilized after the first antibody complex has been formed but prior to contacting the complex with the detection antibody. Materials for solid supports are well known in the art and include, inter alia, commercially available polysaccharide matrices selected from the group consisting of: sepharose, sephadex; agarose, sephacell, micro-cellulose, and alginate-beads, polypeptide matrices, polystyrene beads, latex beads, magnetic beads, colloid metal particles, glass, plastic and/or silicon chips and surfaces, nitrocellulose strips, membranes, sheets, duracytes, wells and walls of reaction trays, plastic tubes. In an aspect of the invention, said solid support is made of gamma-irradiated polysterene.

The term "first antibody-complex" refers to a complex comprising the first capture antibody specifically bound to the processed, partially processed, or unprocessed Neurotoxin polypeptides. The said antibody-complex is formed as the result of contacting the first capture antibody with the solution comprising the said processed, partially processed and/or unprocessed Neurotoxin polypeptides as set forth above.

According to the method of the invention, the "second capture antibody" specifically binds to an epitope which comprises the linker of unprocessed and/or partially processed Neurotoxin polypeptide or parts thereof. In cases where a linker sequence is missing, it is envisaged that the said second capture antibody specifically binds to an epitope comprising the uncleaved proteolytic cleavage site or parts thereof. In an aspect of the invention, the second capture antibody does not cross react with the processed Neurotoxin polypeptide to a significant extent. In an aspect, said second immobilized capture antibody specifically binds to an epitope essentially consisting of, comprising or being comprised by an amino acid sequence as shown in SEQ ID NO: 1 to 16, see Table 2 or 3 below.

TABLE 2

Amino acid sequences of the cleavage sites of different Neurotoxin polypeptides and flanking sequences

| SEQ ID NO: | Sequence of the epitope including cleavage sites (highlighted) | Neurotoxin (Bacterial Strain) |
|---|---|---|
| 1 | KLLCVRGIITSKTKSLDKGYNKALN....DLCIKV | BoNT/A (Hall/62A) |
| 2 | IQMCKSVKAPG................ICIDV | BoNT/B (Okra) |
| 3 | TKFCHKAIDGRSL....YNKTL......DCRELLV | BoNT/C1 (C-6814) |
| 4 | TKVCLRLTK........NSRD......DSTCIKV | BoNT/D |
| 5 | IRFCKNIVSVKG......IRK........SICIEI | BoNT/E (Beluga) |
| 6 | VKFCKSVIPRKG......TKAP......PRLCIRV | BoNT/F (NCTC10281) |
| 7 | IAMCKPVMYKNT......GKS........EQCIIV | BoNT/G |
| 8 | IGLCKKIIPPTNIRENLYNRTASLTDLGGELCIKI | TeNT |

TABLE 3

Amino acid sequences of the linker regions

| SEQ ID NO: | Sequence of the epitopes | Cleavage sites | Neurotoxin/ Bacterial Strain |
|---|---|---|---|
| 9 | TKSLDKGYNK | K438/T439 K448/A449 | BoNT/A (Hall/62A) |
| 10 | CKSVKAPGIC | K441/A442 | BoNT/B (Okra) |
| 11 | SLYNK | R444/S445 K449/T450 | BoNT/C1 (C-6814) |
| 12 | NSR | K442/N443 R445/D446 | BoNT/D (CB16) |
| 13 | GIR | K419/G420 R422/K423 | BoNT/E (Beluga) |
| 14 | KGTK | R435/K436 K439/A440 | BoNT/F (NCTC10281) |
| 15 | NGTK | | BoNT/G |
| 16 | ENLYNR | R449 (alternatively R455) | TeNT |

Due to the presence of the aforementioned epitope, the unprocessed or partially processed Neurotoxin polypeptides can be specifically bound by the second capture antibody, and, thus, form a second antibody-complex. The said second capture antibody is, in an aspect, immobilized as explained in detail above.

Accordingly, the term "second antibody-complex" refers to a complex comprising the second capture antibody specifically bound to partially processed or unprocessed Neurotoxin polypeptide. The said second antibody-complex, however, shall not comprise processed Neurotoxin polypeptide.

According to the method of the invention, the "detection antibody" specifically binds to the first and/or second antibody-complex. In an aspect, the detection antibody for the first and the second antibody-complex is identical. However, in a further aspect, different detection antibodies may be used for the first and the second antibody-complex. In an aspect, the detection antibody specifically binds to epitopes on the heavy chain of the processed, partially processed and unprocessed Neurotoxin polypeptide. Due to the presence of the same epitope in both complexes, the first antibody-complex or the second antibody-complex can be specifically bound and, thus, be detected by the detection antibody in said aspect of the invention.

As a result of the specific binding of the detection antibody, a first detection complex or a second detection complex is formed, respectively.

Therefore, the term "first detection complex" refers to a complex comprising the first antibody-complex and the detection antibody. Likewise, the term "second detection complex" refers to a complex comprising the second antibody-complex and the detection antibody.

In an aspect of the method of the invention, said detection antibody comprised by the first or second detection complex is coupled to a detectable label allowing the measurement of the amount of the detection antibody which is bound to the detection complex. By measuring the said amount of bound detection antibody, the amount of first or second antibody-complexes can be determined since the amount of bound detection antibody in the detection complex correlates with the amount of antibody-complex comprised by the detection complex. Labeling may be done by direct or indirect methods. Direct labeling involves binding of the label directly (covalently or non-covalently) to the first detection antibody. Indirect labeling involves binding (covalently or non-covalently) of an agent which specifically binds to the detection antibody and which carries a detectable label. Such an agent may be, e.g., a secondary (higher order) antibody which specifically binds to the detection antibody. The secondary antibody in such a case will be coupled to a detectable label. It will be understood that further higher order antibodies can be used in addition for detection of the detection complex. The higher order antibodies are often used to increase the signal. Suitable higher order antibodies may also include the well-known streptavidin-biotin system (Vector Laboratories, Inc.), and the well-known Dako LSAB™2 and LSAB™+ (labeled streptavidin-biotin), or Dako PAP (Peroxidase Anti-Peroxidase). In a further aspect, the said label of the first detection antibody is selected from the group consisting of: fluorescent dyes, chemoluminescent molecules, radioactive labels and enzymes capable of generating a detectable signal. Typical fluorescent labels include fluorescent proteins (such as GFP and its derivatives), Cy3, Cy5, Texas Red, Fluorescein, and the Alexa dyes (e.g. Alexa 568). Typical radioactive labels include $^{35}S$, $^{125}I$, $^{32}P$, $^{33}P$ and the like. Alternatively, a detectable label coupled to the said first detection antibody may also be an enzyme which is capable of generating a detectable signal, e.g., by conversion of a substrate. In an aspect, such an enzyme may be a peroxidase (e.g., horseradish peroxidase) or alkaline phosphatase.

The term "determining the amount" as used herein relates to measuring the absolute amount, relative amount or concentration in a quantitative or semi-quantitative manner. Measuring will be done based on the chemical, physical or biological properties of the detectable label coupled to the first detection antibody. Suitable measures for detection are well known to those skilled in the art and depend on the nature of the detectable label as set forth above. It will be understood, however, that the amount of detectable label which can be measured correlates directly to the amount of detection complex which again correlates to the amount of antibody complex and, thus, to the amount of the Neurotoxin species to be determined, i.e. to either the total (processed, unprocessed and partially processed Neurotoxin) or the unprocessed and partially processed Neurotoxin. It will be understood that the determination of the amount of Neurotoxin polypeptides, in an aspect, also requires calibration of the method by applying standard solutions with predefined amounts of Neurotoxin polypeptides. How to carry out such a calibration is well known to those skilled in the art.

The term "calculating" as used in accordance with the method of the present invention relates to mathematical operations which allow for determining the amount of processed Neurotoxin based on the amounts of total Neurotoxin (i.e. processed, unprocessed and partially processed Neurotoxin) and the amount of partially processed and unprocessed Neurotoxin. In an aspect of the method of the present invention, said calculating includes subtraction of the amount of partially processed and unprocessed Neurotoxin from the amount of total Neurotoxin.

Advantageously, the method of the present invention allows for a reliable determination of the amount of processed Neurotoxin in a given preparation. Accordingly, the quality of Neurotoxin preparations can be increased since the preparations can be tested for constant amounts of the desired processed Neurotoxin polypeptide.

In principle, the method of the present invention can be carried out by coupling a first capture antibody to a solid support such as a reaction vial. Similarly, the second capture antibody shall be coupled to another physically separate solid support (e.g., a further reaction vial). Both capture antibodies coupled to the solid supports will subsequently be brought into contact to the said portions of the solution comprising the processed, unprocessed and/or partially processed Neurotoxin to be determined. Such a solution could be, e.g., a purified bacterial cell culture from *Clostridum* sp. It will be understood that a first portion will be brought into contact with the first capture antibody on the first solid support and the second portion will be brought into contact with the second capture antibody on the second solid support. The portions are usually of equal volume and are normalized with respect to their contents, e.g., their total protein content. Contacting will be carried out for a time sufficient to allow specific binding of the first and second capture antibodies to their respective antigens. For example, contacting can be carried out at room temperature for approx. an hour. Subsequently, the first and second portion of the solution will be discarded and the solid supports (e.g., reaction vials) will be washed once or twice by a buffer under conditions which do not affect the first and second antibody-complexes which have been meanwhile formed with the capture antibodies on the solid supports. After the washing steps have been carried out, the (first) detection antibody will be added to the solid supports under conditions which allow for specific binding of the detection antibody. Excess detection antibody shall be removed by further washing steps using an appropriate buffer. Subsequently, the amount of the first and the second detection complex can be determined by determination of the amount of specifically bound detection antibody. This will be achieved dependent on the nature of the label of the detection antibody, e.g., by measuring the optical density or the intensity of fluorescence. The measured amount for the detectable label can be compared with calibration standards in order to determine the amount of a Neurotoxin species, i.e. either the total (processed, unprocessed and partially processed Neurotoxin) or the unprocessed and partially processed Neurotoxin in the first or second detection complex. It will be understood that the first detection complex represents the amount of total Neurotoxin while the second detection complex represents the amount of partially processed and unprocessed Neurotoxin polypeptides, only. Accordingly, the amount of processed Neurotoxin polypeptide can be calculated in the aforementioned setup by subtracting the amount of the partially processed or unprocessed Neurotoxin polypeptide from the total Neurotoxin polypeptide amount.

It is to be understood that the definitions and explanations of the terms made above apply mutatis mutandis for all aspects described in this specification in the following except as otherwise indicated.

The present invention also relates to a method for the determination of the amount of processed (active) Neurotoxin polypeptide in a solution comprising processed Neurotoxin polypeptide and partially processed and/or unprocessed Neurotoxin polypeptide comprising the steps of:

a) contacting a first portion of said solution with a first capture antibody which specifically binds to the heavy chains of mature Neurotoxin polypeptide, partially processed, and unprocessed Neurotoxin polypeptide under conditions which allow for binding of said antibody to said mature Neurotoxin, partially processed, and unprocessed Neurotoxin polypeptide, thus forming a first antibody-complex, b) contacting the first antibody complex with a detection antibody which specifically binds to the light chain of said mature Neurotoxin, partially processed, and unprocessed Neurotoxin polypeptide in the antibody complex formed in step a), whereby a first detection complex is formed, c) contacting a second portion of said solution with a second capture antibody which specifically binds to the linkers of said partially processed and unprocessed Neurotoxin polypeptide under conditions which allow for binding of said antibody to said partially processed and unprocessed Neurotoxin polypeptide, and thus forming a second antibody-complex, d) contacting the second antibody-complex with the detection antibody, whereby a second detection complex is formed, e) determining the amount of the second detection complex formed in step b) and step e), and f) calculating the amount of mature Neurotoxin polypeptide based on the amounts of the first and second detection complex determined in step e).

In another aspect of the methods of the invention, said methods further comprises determining the binding activity of Neurotoxin polypeptide.

The term "binding activity" as used in accordance with the method of the invention relates to the capability of the processed Neurotoxin polypeptide to a surface receptor protein which is present, e.g., on peripheral cholinergic nerve endings. Receptor proteins include in aspect SV2 for BoNT/A, synaptotagmins I and II for BoNT/B and BoNT/G, and a ganglioside ($GT_{1B}$) coreceptor. In an aspect of the method of the invention, said binding activity can be determined ex vivo using a model substrate which substitutes the surface protein receptor by mimicking its binding domain. Said model substrate is, in an aspect, a labeled peptide derived from the aforementioned receptor proteins. In a further aspect, suitable labels include those mentioned elsewhere in this specification, and, in particular, biotin.

Thus, the present invention also contemplates a method for determining the binding activity of a Neurotoxin polypeptide comprising the steps of a) contacting a portion of a Neurotoxin polypeptide containing solution with a labeled peptide, whereby a complex is formed, and b) determining the said complex formed in step (a) based on the label, whereby the presence or absence of the complex or its amount is indicative for the binding activity of the Neurotoxin polypeptide in said solution.

The complex can be determined based on the nature of the label which has been used to label the peptide. In an aspect, e.g., the biotinylated peptide comprised by a complex can be determined by a Streptavidin conjugate capable of generating a detectable signal. The presence, absence or intensity will be indicative for the binding activity of the Neurotoxin polypeptides in the solution or its strength.

In another aspect of the method of the invention, said method further comprises determining the proteolytic activity of Neurotoxin polypeptide.

The term "proteolytic activity" as used in accordance with the method of the invention relates to the capability of processed Neurotoxin to proteolytically cleave N-ethylmaleimide-sensitive attachment receptor (SNARE) proteins involved in synaptic vesicle membrane fusion. In an aspect, said cleavage is zinc(II)-dependent. The said proteolytic activity can be determined using a model substrate which substitutes a naturally occurring SNARE protein. Moreover, upon cleavage, a detectable label such as a dye shall be released from the said model substrate. In one aspect, the model substrate is a compound having the general formula X-para-Nitroanilid, wherein X is Arginine or peptide having the sequence Arginine-Y, wherein Y represents one or more amino acids, and in another aspect, the compound is Arginine-para-Nitroanilid.

Thus, the present invention further contemplates a method for determining the proteolytic activity of a Neurotoxin comprising the steps of a) contacting a portion of a Neurotoxin polypeptide containing solution with a compound having the general formula: X-para-Nitroanilid, wherein X is Arginine or a peptide having the sequence Arginine-Y, wherein Y represents one or more amino acids, and b) determining the proteolytic activity of Neurotoxin polypeptide in said solution based on the amount of released para-Nitroaniline from step b) which correlates to the amount of Neurotoxin polypeptide.

In an aspect, Y represents a peptide residue having an amino acid sequence as shown in any one of SEQ ID NOs: 25 or 26.

The processed Neurotoxin polypeptide comprised by the said portion of the solution can cleave and, thus, release para-Nitroaniline from the remaining peptide. Para-Nitroaniline is a dye well known in the art. Determining the proteolytic activity of Neurotoxin polypeptide in said solution is based on the amount of released para-Nitroaniline which correlates to the amount of Neurotoxin polypeptide.

The present invention also contemplates a device for determining the amount of processed Neurotoxin polypeptide in a solution comprising:

a) an arrangement of a first capture antibody, a second capture antibody and a detection antibody, wherein said arrangement allows for carrying out the steps a) to e) of the aforementioned methods; and b) means for calculating the amount of mature Neurotoxin polypeptide based on the amounts of the first and second detection complex determined by the arrangement according to a).

The term "device" as used herein relates to a system comprising at least the aforementioned arrangement and means operatively linked to each other as to allow the determination. In an aspect, the arrangement can be a solid support with immobilized capture antibodies as referred to above which may be present in physically separate vials in order to allow a separate contacting with the first and second portion of the solution. Moreover, the device may comprise, in an aspect, a unit for the determination of the amount of the detection complexes. Dependent on the kind of detection antibody to be used, such a unit will comprise a detector for the signals generated by the detection antibody. Moreover, the unit can also comprise, in an aspect, means for calibration, e.g., a computer based algorithm, for comparing the measured signals to the calibration standards in order to determine the amounts of the Neurotoxin polypeptides present in a solution or portion thereof. The device will also comprise means for calculating the amount of mature Neurotoxin polypeptide based on the amounts of the first and second detection complex, e.g., a computer-based algorithm for carrying out the calculation.

Further, the invention relates to a kit adapted for carrying out the aforementioned methods, said kit comprising:
a) an arrangement of a first capture antibody, a second capture antibody and a detection antibody, wherein said arrangement allows for carrying out the steps a) to e) of the aforementioned methods;
b) means for calculating the amount of mature Neurotoxin polypeptide based on the amounts of the first and second detection complex determined by the arrangement according to a); and
c) instructions for carrying out said method.

The term "kit" as used herein refers to a collection of the aforementioned means or reagents of the present invention which may or may not be packaged together. The components of the kit may be comprised by separate vials (i.e. as a kit of separate parts) or provided in a single vial. Moreover, it is to be understood that the kit of the present invention is to be used for practicing the methods referred to herein above. In one aspect, it is envisaged that all components are provided in a ready-to-use manner for practicing the methods referred to above. In a further aspect, the kit contains instructions for carrying out the said methods. The instructions can be provided by a user manual in paper- or electronic form. For example, the manual may comprise instructions for interpreting the results obtained when carrying out the aforementioned methods using the kit of the present invention.

All references cited in this specification are herewith incorporated by reference with respect to their entire disclosure content and the disclosure content specifically mentioned in this specification.

FIGURES

Figure 1:
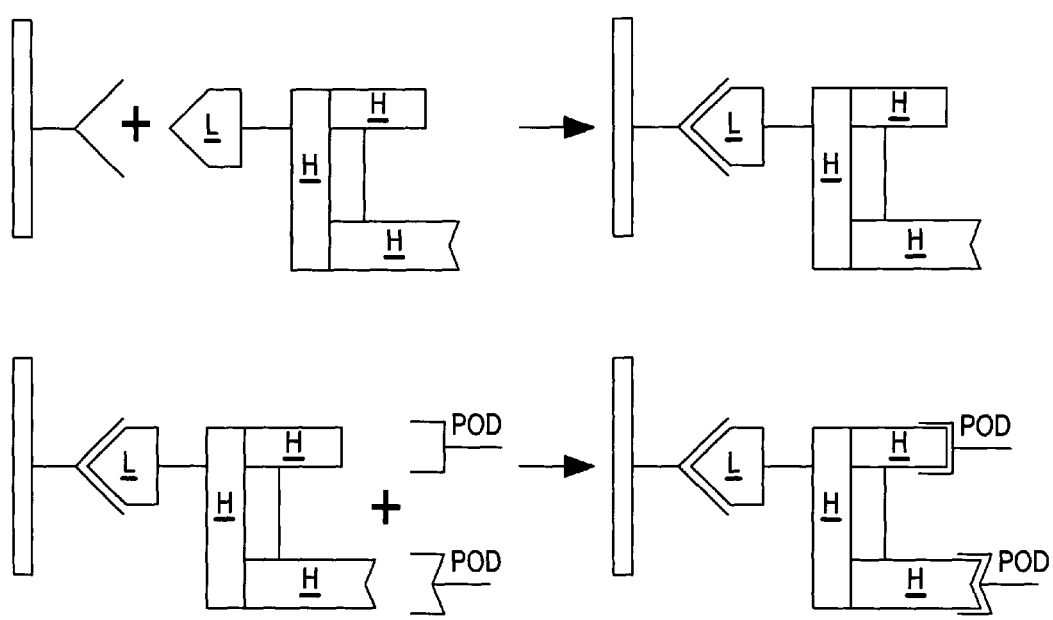

FIG. 1: Scheme of the binding of at least one (or more) detection antibody.

Figure 2:
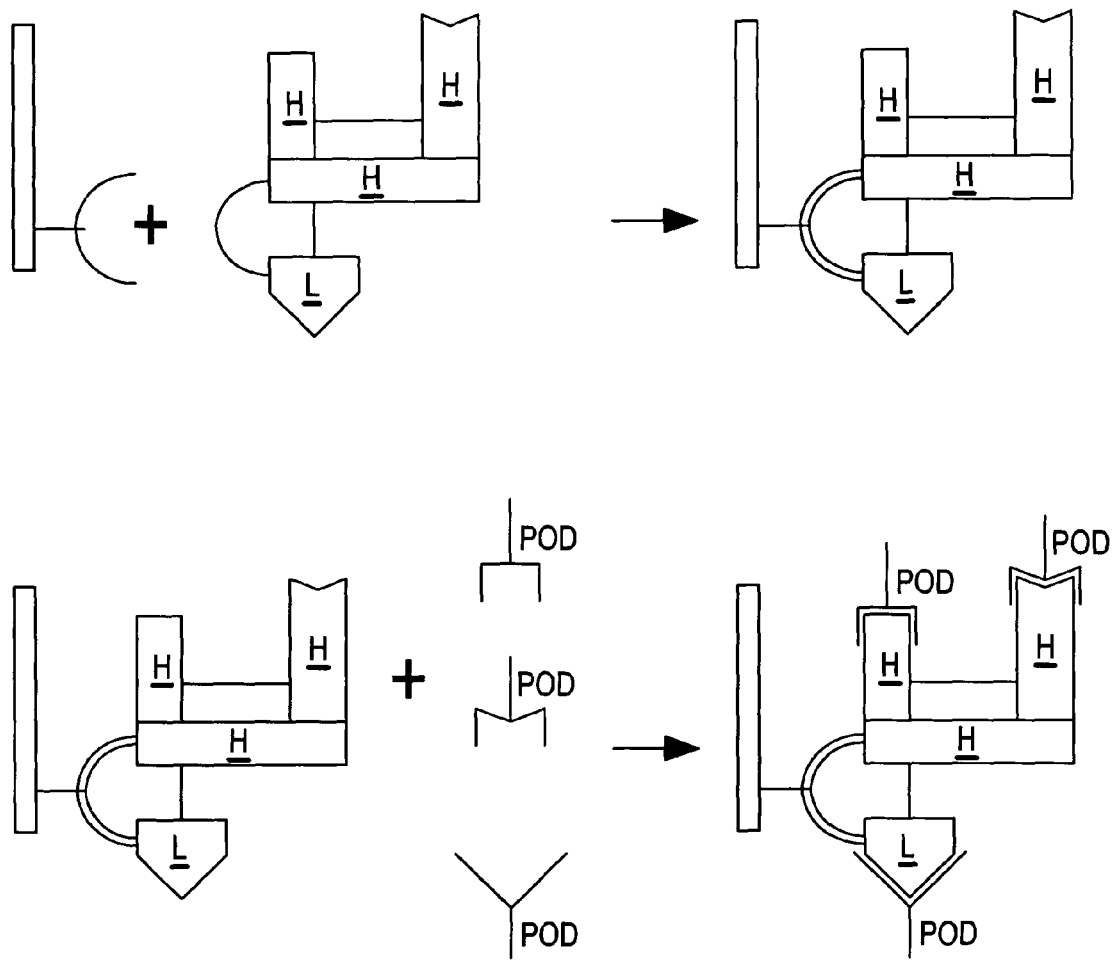

FIG. 2: Scheme of the specific binding of the second capture antibody to the partially processed or unprocessed precursor Neurotoxin polypeptide and the subsequent binding of at least one (or more) detection antibody.

FIG. 3: Scheme of the determination of the binding activity of the Neurotoxin polypeptide.

Figure 4:
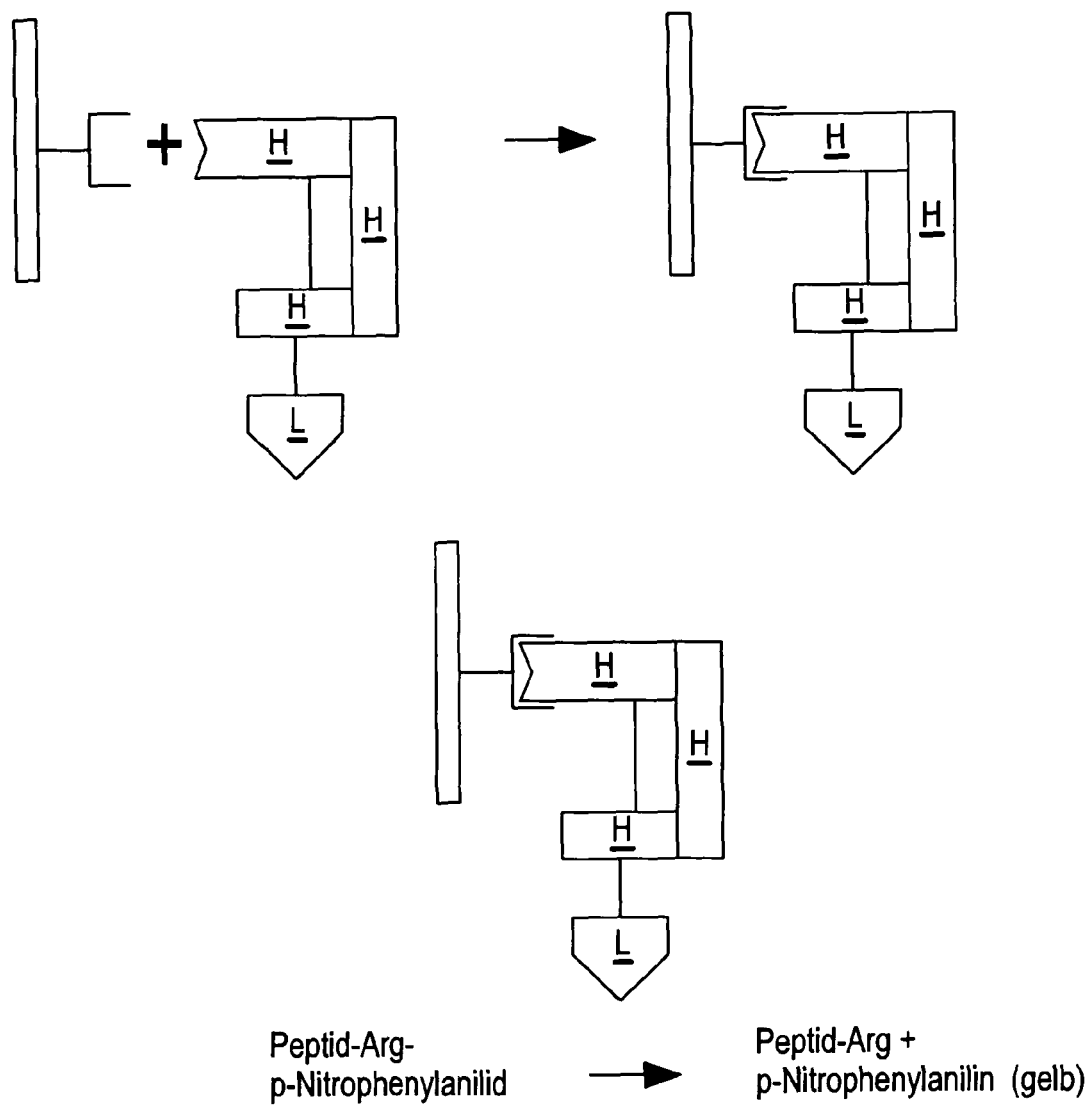

FIG. 4: Scheme of the determination of the proteolytic activity of the Neurotoxin polypeptide.

The invention claimed is:

1. A method for determining the amount of processed neurotoxin polypeptides in a solution comprising processed neurotoxin polypeptides and partially processed and/or unprocessed neurotoxin polypeptides comprising the steps of:
   a) contacting a first portion of the solution with a first capture antibody which specifically binds to light chains of processed, partially processed and unprocessed neurotoxin polypeptides under conditions which allow for binding of the antibody to the neurotoxin polypeptides, thereby forming a first antibody-complex;
   b) contacting the first antibody complex—with a detection antibody which specifically binds to heavy chains of the processed, unprocessed and partially processed neurotoxin polypeptides in the antibody complex formed in step a), whereby a first detection complex is formed;
   c) contacting a second portion of the solution with a second capture antibody which specifically binds to the linker of partially processed or unprocessed neurotoxin polypeptides under conditions which allow for binding of the antibody to the partially processed or unprocessed neurotoxin polypeptides, thereby forming a second antibody-complex;
   d) contacting the second antibody-complex with the detection antibody which specifically binds to heavy chains of the processed, unprocessed and partially processed neurotoxin polypeptides in the antibody complex formed in step c), whereby a second detection complex is formed;
   e) determining the amount of the first detection complex formed in step b) and the amount of second detection complex formed in step d) by a determination of the amount of specifically bound detection antibody, and
   f) calculating the amount of processed neurotoxin polypeptides based on the amounts of the first and second detection complex determined in step e) by subtracting the amount of the second detection complex from the amount of the first detection complex, thereby determining the amount of processed neurotoxin.

2. The method of claim 1, wherein the first capture antibody is immobilized.

3. The method of claim 1, wherein the second capture antibody is immobilized.

4. The method of claim 1, wherein the second capture antibody specifically binds to a peptide epitope having an amino acid sequence as set forth in any one of SEQ ID NOs: 1 to 16.

5. The method of claim 1, wherein a neurotoxin polypeptide is selected from:
   a) a neurotoxin polypeptide as set forth in any one of SEQ ID NOs: 17 to 24.

6. The method of claim 1, further comprising the step of determining the binding activity of the neurotoxin polypeptide.

7. The method of claim 6, comprising the steps of:
   a) contacting a portion of a solution containing neurotoxin polypeptides with a labeled peptide, whereby a complex is formed, and
   b) determining the amount of complex formed in step a) based on the label, whereby the presence or absence of the complex, or its amount, is indicative for the binding activity of the neurotoxin polypeptide in the solution.

8. The method of claim 1, further comprising the step of determining the proteolytic activity of neurotoxin polypeptides.

9. The method, of claim 8, comprising the steps of:
   a) contacting a portion of a solution comprising neurotoxin polypeptides with a compound having the general formula: X-para-Nitroanilid, wherein X is Arginine or a peptide having the sequence Arginine-Y, wherein Y represents one or more amino acids, and
   b) determining the proteolytic activity of neurotoxin polypeptides in the solution based on the amount of released para-Nitroaniline from step a) which correlates to the amount of neurotoxin polypeptide.

10. A method for determining the amount of processed active neurotoxin polypeptides in a solution comprising processed neurotoxin polypeptides, partially processed and/or unprocessed neurotoxin polypeptides comprising the steps of:
   a) contacting a first portion of the solution with a first capture antibody which specifically binds to the heavy chains of mature neurotoxin polypeptides, partially processed, and unprocessed neurotoxin polypeptides under conditions which allow for binding of the antibody to the mature neurotoxin, partially processed, and unprocessed neurotoxin polypeptides, thereby forming a first antibody-complex,
   b) contacting the first antibody complex with a detection antibody which specifically binds to the light chain of the mature neurotoxins, partially processed, and unprocessed neurotoxin polypeptides in the antibody complex formed in step a), whereby a first detection complex is formed,
   c) contacting a second portion of the solution with a second capture antibody which specifically binds to the linkers of the partially processed and unprocessed neurotoxin polypeptides under conditions which allow for binding of the antibody to the partially processed and unprocessed neurotoxin polypeptides, thereby forming a second antibody-complex,
   d) contacting the second antibody-complex with the detection antibody, whereby a second detection complex is formed,
   e) determining the amount of the first detection complex formed in step b) and the amount of second detection complex formed in step d) by a determination of the amount of specifically bound detection antibody, and
   f) calculating the amount of mature neurotoxin polypeptides based on the amounts of the first and second detection complex determined in step e) by subtracting the amount of the second detection complex from the amount of the first detection complex.

11. The method of claim 10, wherein the first capture antibody is immobilized.

12. The method of claim 10, wherein the second capture antibody is immobilized.

13. The method of claim 10, wherein the second capture antibody specifically binds to a peptide epitope having an amino acid sequence as set forth in any one of SEQ ID NOs: 1 to 16.

14. The method of claim 10, wherein a neurotoxin polypeptide is selected from:
   a) a neurotoxin polypeptide as set forth in any one of SEQ ID NOs: 17 to 24.

15. The method of claim 10, further comprising a step of determining the binding activity of neurotoxin polypeptide.

16. The method of claim 15, comprising the steps of:
   a) contacting a portion of a solution comprising a neurotoxin polypeptide with a labeled peptide, whereby a complex is formed, and
   b) determining the amount of complex formed in step a) based on the label, whereby the presence or absence of the complex or its amount is indicative for the binding activity of the neurotoxin polypeptide in the solution.

17. The method of claim 10, further comprising a step of determining the proteolytic activity of neurotoxin polypeptides.

18. The method of claim 17, comprising the steps of:
a) contacting a portion of a solution comprising neurotoxin polypeptides with a substrate having the general formula: X-para-Nitroanilid, wherein X is Arginine or peptide having the sequence Arginine-Y, wherein Y represents one or more amino acids, and
b) determining the proteolytic activity of the neurotoxin polypeptide based on the amount of para-Nitroaniline released from the substrate which correlates with the amount of neurotoxin polypeptide in the solution.

* * * * *

UNITED STATES PATENT AND TRADEMARK OFFICE
CERTIFICATE OF CORRECTION

PATENT NO. : 8,663,942 B2
APPLICATION NO. : 13/138948
DATED : March 4, 2014
INVENTOR(S) : Michael Pfeil and Josef Friedrich It is certified that error appears in the above-identified patent and that said Letters Patent is hereby corrected as shown below:

Title Page, Other Publications: "Campbell, 1993, Biochim Siophys Acta"
should be
--Campbell, 1993, Biochim Biophys Acta--

Title Page, Other Publications: "Rasooly Reuven, et al., Applied and Environmnetal Microbiology"
should be
--Rasooly Reuven, et al., Applied and Environmental Microbiology--

Signed and Sealed this
Third Day of June, 2014

Michelle K. Lee
*Deputy Director of the United States Patent and Trademark Office*